(12) United States Patent
Dubois et al.

(10) Patent No.: US 7,667,851 B2
(45) Date of Patent: Feb. 23, 2010

(54) METHOD AND APPARATUS FOR USING A TWO-WAVE MIXING ULTRASONIC DETECTION IN RAPID SCANNING APPLICATIONS

(75) Inventors: Marc Dubois, Clifton Park, NY (US);
Thomas E. Drake, Fort Worth, TX (US);
Robert J. Filkins, Niskayuna, NY (US);
Peter W. Lorraine, Niskayuna, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 10/060,983

(22) Filed: Jan. 30, 2002

(65) Prior Publication Data

US 2003/0020923 A1    Jan. 30, 2003

Related U.S. Application Data

(60) Provisional application No. 60/307,478, filed on Jul. 24, 2001.

(51) Int. Cl.
*G01B 11/02* (2006.01)
(52) U.S. Cl. .................................... 356/502
(58) Field of Classification Search ............... 356/486, 356/492, 493, 498, 502, 432; 73/655, 657
See application file for complete search history.

(56) References Cited

U.S. PATENT DOCUMENTS 4,046,477 A     9/1977   Kaule ......................... 356/109

(Continued)

FOREIGN PATENT DOCUMENTS

EP           0217694 A1     5/1988

(Continued)

OTHER PUBLICATIONS

Ing, R. K., et al.; Ultrasound Detection on Rough Surfaces Using Heterodyne Photorefractive Interferometer: Applications to NDE; 1996 IEEE Ultrasonics Symposium; pp. 681-684.

(Continued)

*Primary Examiner*—Michael A Lyons
(74) *Attorney, Agent, or Firm*—Bracewell & Giuliani LLP

(57) ABSTRACT

The invention is directed to a wave characteristic adjusting device used to compensate for a wave characteristic distortion caused by the scanning motion of a probe beam of a two-wave mixing interferometer. The invention is also directed to an apparatus and method for using the wave characteristic adjusting device in a rapid scanning laser ultrasound testing device. In a rapid scanning laser ultrasound testing device, a laser pulse is directed at periodic points along a path across the surface of a manufactured object. The laser pulse initiates an ultrasonic signal associated with the manufactured object. An interferometer may be used to measure the initiated ultrasonic signal. The interferometer scans a probe beam along a path similar to the sonic initiating laser. A pulse of the probe beam is directed at the manufactured object in the vicinity of the initiating laser pulse while continuously scanning. As a result, the probe beam pulse may exhibit a Doppler shift. This Doppler shift may cause a loss in sensitivity of the two-wave mixing interferometer. The wave characteristic adjusting device may be used to compensate for the Doppler shift, thereby improving the sensitivity of the two-wave mixing interferometer.

38 Claims, 17 Drawing Sheets

U.S. PATENT DOCUMENTS

| | | | | |
|---|---|---|---|---|
| 4,475,394 | A | 10/1984 | Takeda et al. | 73/598 |
| 4,530,603 | A | 7/1985 | Shaw et al. | 356/345 |
| 5,018,808 | A | 5/1991 | Meyers et al. | 350/6.91 |
| 5,131,748 | A | 7/1992 | Monchalin et al. | 356/349 |
| 5,146,776 | A | 9/1992 | Twerdochlib et al. | 73/1 DV |
| 5,229,832 | A | 7/1993 | Gaynor | 356/360 |
| 5,507,185 | A | 4/1996 | Pickens | 73/620 |
| 5,680,212 | A * | 10/1997 | Blouin et al. | 356/458 |
| 5,701,003 | A | 12/1997 | Chisholm et al. | 250/205 |
| 6,041,020 | A | 3/2000 | Caron et al. | 367/149 |
| 6,075,603 | A | 6/2000 | O'Meara et al. | 356/358 |
| 6,078,384 | A | 6/2000 | Dammann et al. | 356/28.5 |
| 6,087,652 | A | 7/2000 | O'Meara et al. | 250/214.1 |
| 6,264,607 | B1 | 7/2001 | Goll et al. | 600/437 |
| 2001/0009111 | A1 | 7/2001 | Wortge et al. | 73/657 |

FOREIGN PATENT DOCUMENTS

| | | |
|---|---|---|
| EP | 0251697 A2 | 2/1989 |
| EP | 0486689 A1 | 5/1992 |
| EP | 0493036 A1 | 7/1992 |
| EP | 0494647 A2 | 7/1992 |
| EP | 0642015 A1 | 3/1995 |
| EP | 0669516 A1 | 11/1996 |
| EP | 0840493 A2 | 5/1998 |

OTHER PUBLICATIONS

Klein, Marvin B., et al.; Homodyne Detection of Ultrasonic Surface Displacements Using Two-Wave Mixing in Photorefractive Polymers; 1999 Elsevier Science B.V.; pp. 79-84.

de Montmorillon, Louis-Anne, et al.; Eye-Safe Large Field of View Homodyne Detection Using a Photorefractive CdTe:V Crystal; 1996 Elsevier Science B.V., pp. 293-300.

* cited by examiner

METHOD AND APPARATUS FOR USING A TWO-WAVE MIXING ULTRASONIC DETECTION IN RAPID SCANNING APPLICATIONS

RELATED ART

This application claims priority of U.S. Provisional Application, Ser. No. 60/307,478, filed Jul. 24, 2001 entitled: "Method and apparatus for using a two-wave mixing ultrasonic detection in rapid scanning applications", and is incorporated herein by reference in its entirety.

BACKGROUND OF THE INVENTION

1. Field of the Invention

The present invention generally relates to a method and apparatus for detecting ultrasound signals. In particular, the present invention relates to a method and apparatus for compensating for loss of sensitivity of a two-wave mixing interferometer caused by rapid scanning of a manufactured object or by the relative motion between the inspection system and the manufactured object.

2. Description of Prior Art

Ultrasound testing methods are non-invasive, generally non-destructive, techniques used to measure features of materials. These features may include layer thickness, cracks, delamination, voids, disbonds, foreign inclusions, fiber fractions, fiber orientation and porosity. The features influence a given material's qualities and performance in given applications. Each application places unique demands on the material's qualities including the need for differing strength, flexibility, thermal properties, cost, or ultraviolet radiation resistance. With the changing demands, more non-invasive, non-destructive testing of materials is being performed using techniques such as ultrasound testing.

Ultrasound techniques are applied in research as well as industrial settings. In research, ultrasound techniques are used to test new materials for desired features. The techniques are also used to seek defects in material that has undergone stress or environmental endurance testing. In industry, the techniques are used during scheduled servicing to inspect parts for defects. Aircraft, automobile and other commercial industries have shown increasing interest in these techniques.

As seen in FIG. 1, ultrasound testing uses a sonic energy signal generator 72 to initiate a sonic energy signal 76 about a manufactured object 74. The sonic energy signal 76 is measured by a sonic energy signal measuring device 78. In some cases, a signal analyzer 80 is used to discern features of the manufactured object 74 from the measured sonic energy signal 76.

The sonic energy signal measuring device is often an interferometer. One particular interferometer is a two-wave mixing interferometer. This two-wave mixing interferometer presents the advantages of being simpler, cheaper, and smaller than a Fabry-Perot interferometer. The two-wave mixing interferometer is also less sensitive to laser noise. Additionally, it has a much better low-frequency response than the Fabry-Perot interferometer.

The two-wave mixing interferometer operates by directing a probe beam at the manufactured object and collecting the scattered beam. As seen in FIG. 2, the scattered probe beam 12 is directed at a photo-refractive crystal 16. In the photo-refractive crystal 16, the scattered probe beam 12 in conjunction with a pump beam 14 creates an interference grating. Part of the pump beam 14 is diffracted by the interference grating in the crystal and travels collinearly with the scattered probe beam 12. In one embodiment of a two-wave mixing interferometer, the two beams go directly into a detector 22. In another embodiment, the beams are split into two polarized components by a polarized beam splitter 20. Then, the two polarized components are detected separately by two detectors 22 and 24. A halfwave plate 18 that controls the separation of the polarized components on each detector.

In the photo-refractive crystal, the probe beam 12 and the pump beam 14 interact to form a grating if the optical frequencies of the beams are similar. The grating diffracts part of the pump beam in the same direction as the probe beam. This diffracted pump beam has a phase-front nearly identical to the one of the probe beam. Interference between the two beams is then possible and can be detected by the detector or detectors 22 and 24.

One important parameter of the two-wave mixing interferometer is the grating building time. The grating building time is the time required for the interaction between the two beams to create the optical grating in the crystal. The grating building time is determined by the crystal properties and by the pump beam power.

However, the two-wave mixing interferometer has some drawbacks. The two-wave mixing interferometer is sensitive to target displacements. Two different effects related to the displacement direction can be observed. As seen in FIG. 3, if an axis 34 called "line of sight" is defined as the axis parallel to both the detection laser beam and to the detection optical axis, the target displacement perpendicular to the line of sight is the lateral displacement 38. The target displacement parallel to the line of sight is the normal displacement 40.

The sensitivity of the two-wave mixing interferometer to lateral displacement is directly related to the grating building time. If the target moves laterally, the speckle pattern changes, modifying the phase-front of the probe beam. If the grating building time is small enough, the grating building will be able to follow the phase-front changes and the probe and pump beam will continue to interfere. However, if the grating building time is too long, the quality of the interference between the two beams decreases, decreasing ultrasonic signal quality. The grating building time can be reduced by increasing the power in the pump beam. With increased power, the grating building time values may be low enough to allow the crystal grating to follow speckle pattern changes.

In the case of normal displacements of the target, the displacement induces an optical frequency change in the probe beam (Doppler shift). This difference between the optical frequencies of the probe and pump beams disturbs the grating in the crystal. This problem cannot be solved using practical levels of pump powers. The amplitude of the ultrasonic probe decreases rapidly with the Doppler shift. For example, for an optical wavelength of 1.064 µm and a grating building time of approximately 1 µs, the sensitivity of the two-wave mixing interferometer drops to nearly 0 for an apparent normal velocity of 0.1 m/s.

These two drawbacks limit the use of the two-wave mixing interferometer for laser-ultrasound inspection of complex composite parts. In one exemplary application, there are two lasers involved. One laser generator may be used to initiate a sonic energy signal and one laser may be used for detection. In laser-ultrasound, these two laser beams are scanned along the surface of the sample. The generation laser fires at discrete points. In addition, the detection laser fires at the same points. The two-wave mixing interferometer measures the signal during fractions of seconds after the generation laser fired. The detection laser duration is usually longer than the duration of the initiated ultrasonic signal. Usually, when scanning, the laser beams are not stopped at each measurement point. If the detection laser beam is scanned continuously during the measurement, even only for a few microseconds, there is a change of distance between the measurement point and the laser. This change during the measurement creates an apparent movement of the scanned object.

If the detection laser beam is scanned along the surface of composites having complex shapes, the laser beam scanning effect is similar to sample displacements. An adequate pump power can compensate for the lateral displacement of the laser beam, however, the normal displacement would rapidly render the signal useless. FIG. 4 illustrates the apparent normal displacement while scanning a part 52. The distance from the scanning mirror 56 to the point where the laser probe beam impinges the sample is X. The distance X is parallel to the line of sight of the system. The distance X changes with the scanning mirror angle and the part shape. As the scanning mirror angle varies, the distance changes. The changing distance creates an apparent normal displacement in the part 52. This apparent normal displacement causes an apparent change in frequency. This apparent change in frequency is similar to a Doppler shift. This shift reduces the sensitivity of the two-wave mixing interferometer. As a result, it is difficult to make measurements of sonic energy signals with a two-wave mixing interferometer in a rapid scanning testing system.

As such, many two-wave mixing interferometers suffer from lost sensitivity during rapid scanning. Many other problems and disadvantages of the prior art will become apparent to one skilled in the art after comparing such prior art with the present invention as described herein.

SUMMARY OF THE INVENTION

Aspects of the invention are found in an apparatus for testing physical attributes of a manufactured object. A sonic energy signal generator initiates a sonic energy signal associated with a manufactured object. The sonic energy signal is measured by a sonic energy signal measuring device.

Further aspects of the invention are found in an exemplary apparatus for testing physical attributes of a manufactured object. The apparatus has a wave characteristic adjusting device situated in the path of a test beam. The wave characteristic adjusting device may alter a wave characteristic to compensate for a wave characteristic distortion caused by the scanning motion of a probe beam of a two-wave mixing interferometer. The test beam may be the probe beam or a pump beam of the two-wave mixing interferometer.

In an exemplary embodiment, the probe beam may be scanned across a manufactured object. The probe beam may reflect from the manufactured object with wave characteristic distortions caused by a sonic energy signal associated with the manufactured object. The probe beam may also reflect with a wave characteristic distortion caused by the scanning motion. The wave characteristic adjusting device may adjust the probe beam, the pump beam, or both to compensate for the wave characteristic distortion caused by the scanning motion of the probe beam of the two-wave mixing interferometer.

Another aspect of the invention may be found in an exemplary wave characteristic adjusting device. This exemplary wave characteristic adjusting device may have a micro translator operable to move a mirror in a direction normal to an incident test beam. In doing so, the wave characteristic adjusting device may alter the wave characteristic to compensate for the wave characteristic distortion caused by the scanning motion of the probe beam of the two-wave mixing interferometer.

A further aspect of the invention may be found in another exemplary embodiment of a wave characteristic adjusting device. This wave characteristic adjusting device may have an acousto-optic cell. This acousto-optic cell may be placed in the path of a test beam. The acousto-optic cell may alter the wave characteristic to compensate for the wave characteristic distortion caused by the scanning motion of the probe beam of the two-wave mixing interferometer. The acousto-optic cell may be situated in the path of the probe beam, the pump beam, or both.

In addition, an aspect of the invention may be found in an exemplary embodiment of the wave characteristic adjusting device having more than one acousto-optic cells. In one example, two acousto-optic cells may be placed in series along the path of a test beam. One may adjust the wave characteristic of the test beam by a specific amount in a specific direction. The other may alter the wave characteristic by a differing amount in the opposite direction. In doing so, the test beam is altered to compensate for the wave characteristic distortion caused by the scanning motion of the probe beam of the two-wave mixing interferometer.

Another aspect of the invention may be found in an exemplary embodiment of the wave characteristic adjusting device. The wave characteristic adjusting device may have a polarizer and at least two electro-optic phase modulators. The polarizer may operate in two modes. If the polarizer operates in the first mode, a test beam is directed to the first electro-optic phase modulator. The first electro-optic phase modulator adjusts the phase of the test beam continuously. When the first electro-optic phase modulator reaches a limit, the polarizer shifts into the second mode. Then, the test beam is directed to the second electro-optic phase modulator. The second electro-optic phase modulator adjusts the phase of the test beam continuously. When the second electro-optic phase modulator reaches a limit, the polarizer shifts into the first mode. In this manner, the wave characteristic of the test beam is altered continuously to compensate for the wave characteristic distortion caused by the scanning motion of the probe beam of the two-wave mixing interferometer.

A further aspect of the invention may be found in a system of two coherent electromagnetic energy generators. The coherent electromagnetic energy generators may produce a probe beam and a pump beam for a two-wave mixing interferometer. The pump beam and the probe beam may have a difference in wave characteristics which compensates for the wave characteristic distortion caused by the scanning motion of the probe beam of the two-wave mixing interferometer.

Another aspect of the invention may be found in a system for measuring sonic energy signals associated with a manufactured object. A coherent electromagnetic energy generator may generate a beam of coherent electromagnetic energy. The beam may be used as a probe beam and/or a pump beam in a two-wave mixing interferometer. The probe beam may be scanned across the surface of a manufactured object. A wave characteristic of the probe beam may be altered by scanning the probe beam across the surface of the manufactured object. A wave characteristic adjusting device may be situated in the path of the probe beam, the pump beam, or both. The wave characteristic adjusting device may alter the wave characteristic of a beam to compensate for the wave characteristic distortion caused by the scanning motion of the probe beam of the two-wave mixing interferometer.

This exemplary embodiment may include a wave characteristic controlling system. The wave characteristic controlling system may direct the wave characteristic adjusting device to alter the wave characteristic of a beam. The wave characteristic controlling system may use information from the two-wave mixing interferometer to determine the action of the wave characteristic adjusting device.

This exemplary embodiment may be augmented with a synthetic signal generator. The synthetic signal generator may add a synthetic signal to the probe beam. The wave characteristic controlling system may determine the action of the wave characteristic adjusting device using information associated with the synthetic signal generator. The wave characteristic controlling system may also direct the operation of the synthetic signal generator.

This exemplary embodiment may further have a database. The wave characteristic controlling system may use information from the database to determine the action of the wave characteristic adjusting device. The database may be a representation of the manufactured object.

Further, this exemplary embodiment may have a shape measuring device. This shape measuring device may determine the shape of the manufactured object. The wave characteristic controlling system may determine the action of the wave characteristic adjusting device from information obtained by the shape measuring device.

Further aspects may be found in methods for using the apparatuses, exemplary embodiments, and systems described above. These methods may be determined by the configuration of the systems and apparatuses.

As such, a system for testing manufactured objects with a rapid scanning two-wave mixing interferometer is described. Other aspects, advantages and novel features of the present invention will become apparent from the detailed description of the invention when considered in conjunction with the accompanying drawings.

DETAILED DESCRIPTION OF THE PREFERRED EMBODIMENT

Figure 1:
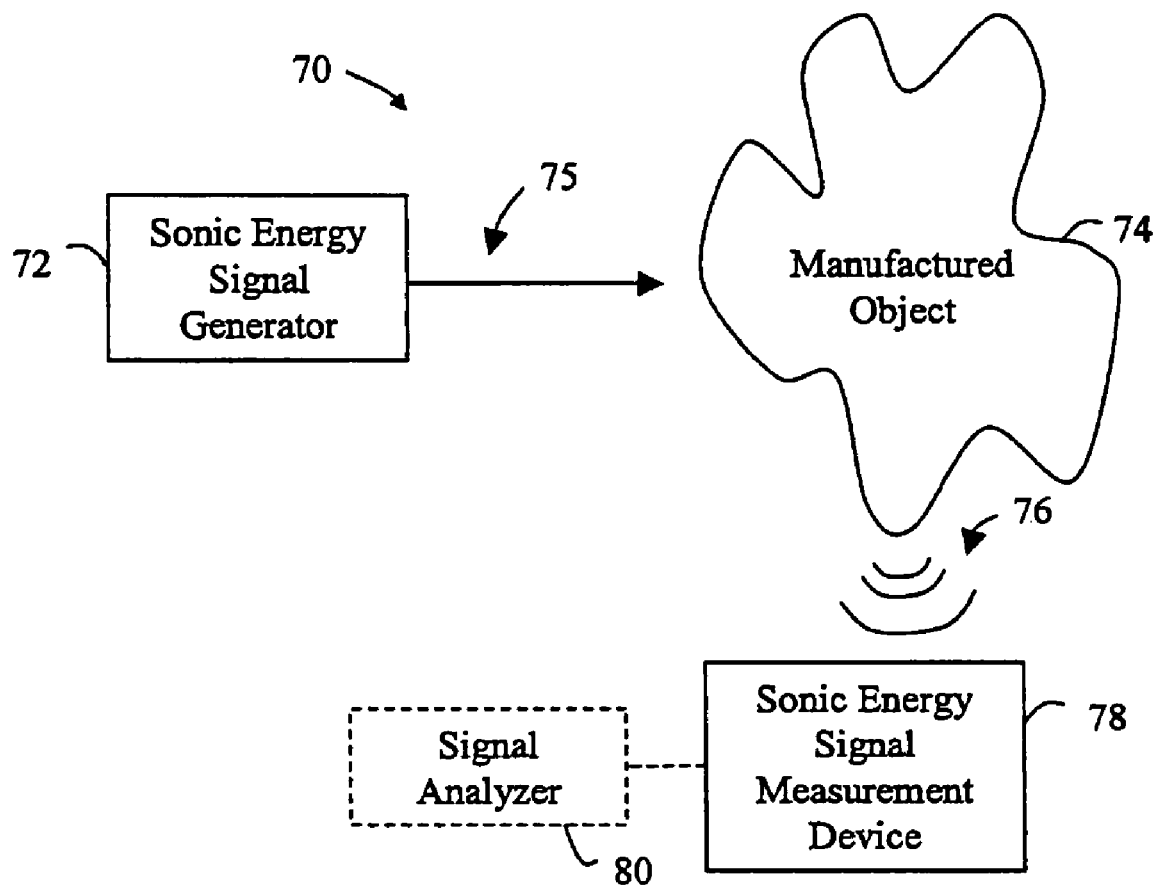
FIG. 1 is a block diagram of a process for testing attributes of a manufactured object according to the invention.

FIG. 1 is a block diagram of a process for testing attributes of a manufactured object according to the invention. As previously described in relation to FIG. 1, a sonic energy signal generator 72 initiates a sonic energy signal 76 about a manufactured object 74. The sonic energy signal is detected by a sonic energy signal measuring device 78. A signal analyzer 80 may be used to discern features of the manufactured object 74 from the sonic energy signal 76.

The sonic energy signal generator 72 may be one or more transducers, a laser generator, a plasma generator, an optical parametric oscillator, or others. In one exemplary embodiment, a laser generator initiates a sonic energy signal 76 by directing a pulse of coherent electromagnetic energy 75 at the manufactured object 74.

Several methods may be used for detection of a sonic energy signal. These methods may include a transducer, a Fabry-Perot laser interferometer, or a gas-coupled laser acoustic detector, to name a few. However, each has known and obvious limitations. Another potential sonic energy signal measuring device is the two-wave mixing interferometer.

Figure 2:
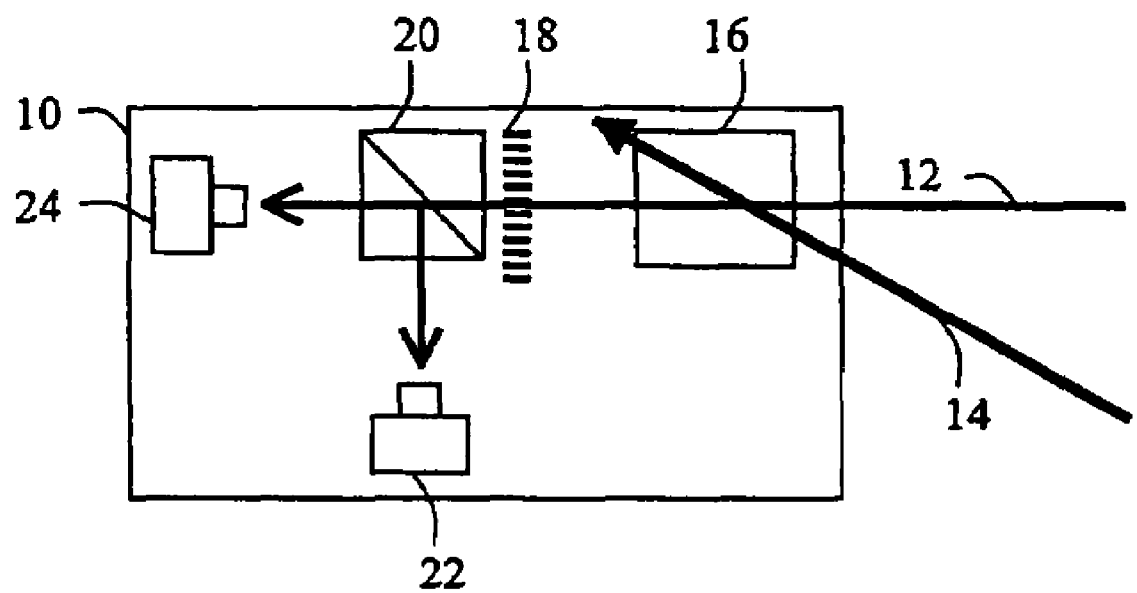
FIG. 2 is block diagram of one embodiment of a two-wave mixing interferometer for use in the process of FIG. 1.

FIG. 2 is block diagram of one embodiment of a two-wave mixing interferometer for use in the process of FIG. 1. The two-wave mixing interferometer may be used to detect small transient motions associated with the manufactured object. These small transient motions may be, for example, a sonic energy signal such as an ultrasound signal.

The two-wave mixing interferometer operates by directing a pump beam 14 and a probe beam 12 at a photo-refractive crystal 16. These beams create a diffraction grating in the crystal 16. The pump beam 14 and the probe beam 12 exit the crystal 16 and are directed to one or more detectors.

The crystal 16 may operate in several ways. One way creates the optimal diffraction grating using a pump beam with a phase shifted $\pm\pi/2\pm2\pi n$ (n is an integer) from the phase of the probe beam. Another way is to apply a voltage across the crystal 16. These crystals 16 can be made from Sillenite type such as BSO, BGO or BTO, or from semiconductors like Gallium Arsenide (GaAs), Indium Phosphide (InP) with iron doping, Cadmium Telluride (CdTe) with vanadium doping with or without an applied electric field, among others.

Figure 3:
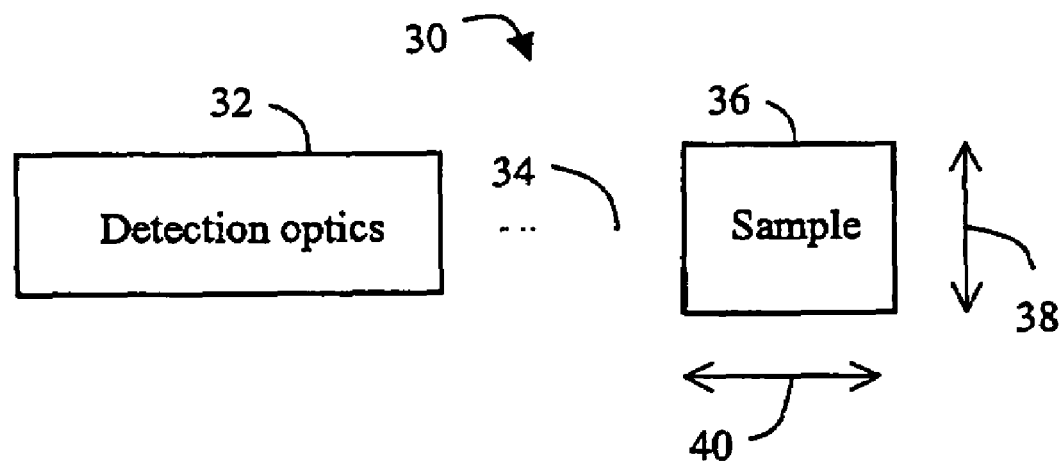
FIG. 3 is a block diagram depicting displacements relevant to the process for testing of FIG. 1.

However, sensitivity of the two-wave mixing interferometer can be lost by motion of the object. This motion may be an actual or apparent effect of the motion of the probe beam. FIG. 3 is a block diagram depicting displacements relevant to the process for testing of FIG. 1. Lateral displacements 38 relative to the "line of sight" axis 34 of the detection optics 32 can be counteracted for by increasing the power of the pump beam. However, normal displacements 40 cause an apparent frequency or Doppler shift in the scattered probe beam. This frequency shift causes a disparity between the scattered probe beam and the pump beam. If this disparity is not corrected, the diffraction grating in the photo-refractive crystal may be lost. As a result, the sensitivity of the two-wave mixing interferometer will be reduced.

Figure 4:
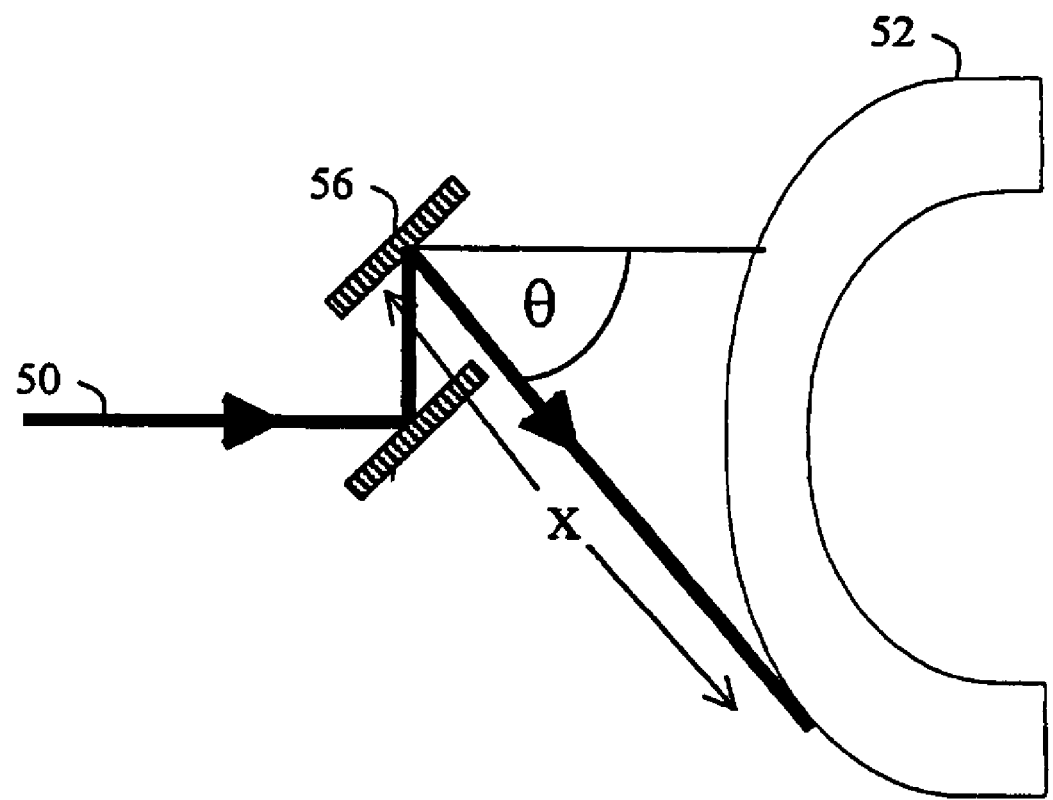
FIG. 4 is a schematic block diagram of a scanning probe beam used by a two-wave mixing interferometer similar to the embodiment of FIG. 2.

An apparent normal displacement can result from the scanning motion of the probe beam used in a rapid scanning test device. FIG. 4 is a schematic block diagram of a scanning probe beam used by a two-wave mixing interferometer similar to the embodiment of FIG. 2. As the scanning mirror 56 directs the probe beam 50 along the surface of the object 52, the distance the probe beam travels to and from the object varies. This variance creates the apparent normal displacement and the frequency shift. The frequency shift causes a disparity between the pump beam frequency and that of the scattered probe beam. This disparity causes a loss in the sensitivity of the two-wave mixing interferometer.

In addition, movement by the object 52 or the detection optics 32 in a normal direction may cause a frequency shift. This normal movement and the apparent normal movement may have acceleration or have a constant velocity. The frequency shift may cause a disparity between the pump beam frequency and that of the scattered probe beam. As such, this disparity may cause a loss in the sensitivity of the two-wave mixing interferometer.

Therefore, it is necessary to compensate for the frequency or Doppler shift caused by either the normal displacement or the apparent normal displacement of the object and/or detection optics. Many potential methods can be used to compensate for the frequency shift of the scattered probe beam. Often, these methods may be applied to the scattered probe beam or the pump beam.

Figure 5:
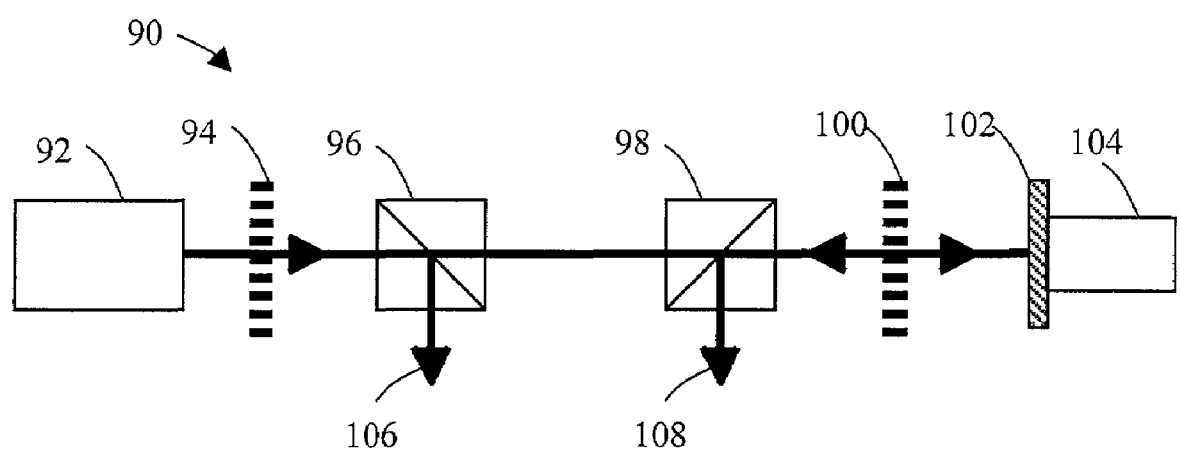
FIG. 5 is a schematic block diagram of an apparatus for compensating for wave characteristic distortions caused by the displacements exemplified in FIG. 3 for use in the testing process of FIG. 1.

One such method is that exemplified in the embodiment shown in FIG. 5. FIG. 5 is a schematic block diagram of an apparatus for compensating for wave characteristic distortions caused by the displacements exemplified in FIG. 3 for use in the testing process of FIG. 1. In this exemplary apparatus 90, a coherent electromagnetic energy generator 92, such as a laser generator, directs a beam of coherent electromagnetic energy through a half wave plate 94. Then, the beam of coherent electromagnetic energy is directed to a beam splitter 96 where a first test beam of coherent electromagnetic energy 106 is split from the generated beam of coherent electromagnetic energy.

The remainder of the generated beam of coherent electromagnetic energy passes through another beam splitter 98. Then, the generated beam of coherent electromagnetic energy passes through a quarter wave plate 100. Next, the generated beam of coherent electromagnetic energy reflects from a mirror 102 attached to a micro translator 104.

The micro translator is operable to move the mirror in a direction normal to the incident direction of the beam of coherent electromagnetic energy. The reflected beam of coherent electromagnetic energy again passes through the quarter wave plate 100 and the beam splitter 98. At the beam splitter, a second test beam of coherent electromagnetic energy 108 is split from the reflected beam of coherent electromagnetic energy. This method for using the exemplary apparatus shown in FIG. 5 results in two test beams of coherent electromagnetic energy 106 and 108 which may compensate for the wave characteristic distortion caused by the scanning motion of a probe beam of a two-wave mixing interferometer.

A wave characteristic may be a frequency profile or a wave phase, among others. A wave characteristic distortion may be a shift in the frequency profile or a shift in the phase, to name a few.

In a typical embodiment, the scanning motion may create an apparent 2 meters per second normal motion of the manufactured object. Therefore, the mirror velocity should be 2 meters per second during the measurement duration. A typical duration for laser-ultrasound measurement is 50 microseconds. The required total displacement of the mirror may therefore be only 100 micrometers.

The first test beam of coherent electromagnetic energy 106 may be either a probe beam or pump beam of a two-wave mixing interferometer. In addition, the second test beam of coherent electromagnetic energy 108 may be either a probe beam or pump beam of a two-wave mixing interferometer.

Several devices may be used to generate the beam of coherent electromagnetic energy. These devices may include any device suitable for generating a beam of coherent electromagnetic energy for use in a two-wave mixing interferometer. These devices are selected from, but not limited to, a Nd:YAG laser, a Yb:YAG laser, a Nd:YVO$_4$ laser, a Nd:YLF laser, a Tm:YLF laser, a Ho:YLF laser, a Ho:YAG laser or any other device that can produce electromagnetic coherent energy like, but not limited to, an optical parametric oscillator or a harmonic generator, among others.

The micro translator may take many forms. These forms may include a piezo-electric translator, an electromagnetic pusher, or any other system providing a controlled normal displacement.

Other similar configurations may result in the compensation for the wave characteristic distortion caused by the scanning motion of a probe beam of a two-wave mixing interferometer. An aspect of these configurations is the motion of a mirror in a direction normal to the incidence of one beam of a two-wave mixing interferometer. Another aspect of these configurations is the mirror moving by a specific amount with a specific velocity for a duration similar to that of the scanning motion of the probe beam.

Figure 6:
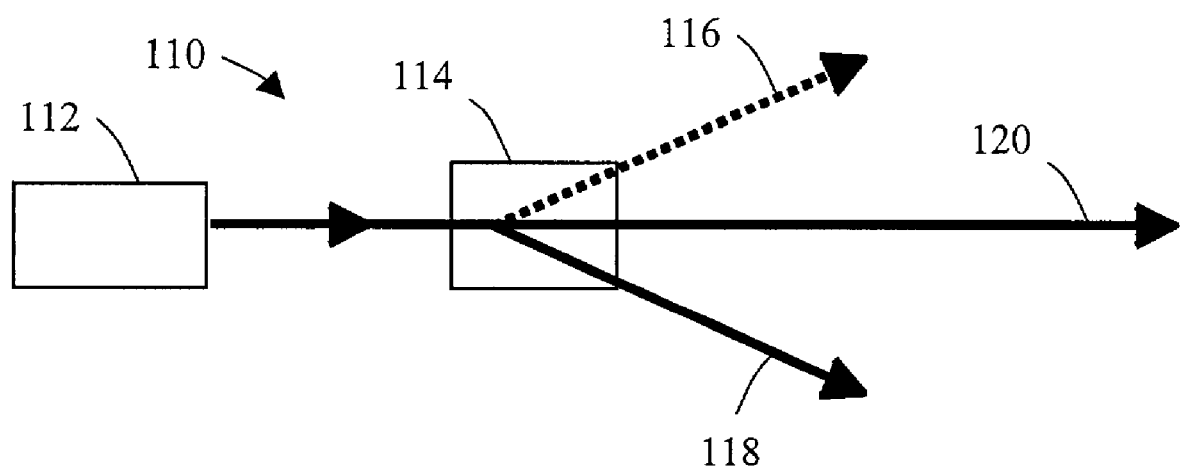
FIG. 6 is a schematic block diagram of another apparatus for compensating for wave characteristic distortions caused by the displacements exemplified in FIG. 3 for use in the testing process of FIG. 1.

FIG. 6 is a schematic block diagram of another apparatus for compensating for wave characteristic distortions caused by the displacements exemplified in FIG. 3 for use in the testing process of FIG. 1. The exemplary apparatus 110 of FIG. 6, uses an acousto-optic cell 114. A coherent electromagnetic energy generator 112, such as a laser generator, directs a beam of coherent electromagnetic energy toward the acousto-optic cell 114. The acousto-optic cell 114 may be used to alter the wave characteristic of the generated beam of coherent electromagnetic energy. For example, the acousto-optic cell 114 may shift the frequency profile of the generated beam to a higher frequency profile, resulting in an altered beam of coherent electromagnetic energy 116. The acousto-optic cell 114 may shift the frequency profile of the generated beam to a lower frequency profile, resulting in an altered beam of coherent electromagnetic energy 118. Further, the acousto-optic cell 114 may not shift the frequency profile, resulting in a beam of coherent electromagnetic energy 120.

The shift of the frequency profile may be adjusted. This adjustment is associated with a wave characteristic of an acoustic wave within the acousto-optic cell 114.

Several devices may be used to generate the beam of coherent electromagnetic energy. These devices may include any device suitable for generating a beam of coherent electromagnetic energy for use in a two-wave mixing interferometer. These devices is selected from, but not limited to, a Nd:YAG laser, a Yb:YAG laser, a Nd:YVO$_4$ laser, a Nd:YLF laser, a Tm:YLF laser, a Ho:YLF laser, a Ho:YAG laser or any other device that can produce electromagnetic coherent energy like, but not limited to, an optical parametric oscillator or a harmonic generator, among others.

The acousto-optic cell 114 may take many forms. These forms may include forms in which a piezo-electric transducer induces acoustic waves in the acousto-optic cell 114, among others. The acousto-optic cell 114 may be made from fused silica, gallium arsenide, gallium phosphide, germanium, lead molybdate, tellurium dioxide, lithium niobate, or any other material useful for altering electromagnetic wave characteristics with acoustic waves.

With the apparatus shown in FIG. 6, a method for compensating for the wave characteristic distortion caused by the scanning motion of a probe beam of a two-wave mixing interferometer may be described. The method may comprise directing the probe beam of the two-wave mixing interferometer toward the acousto-optic cell 114 and inducing, in the acousto-optic cell 114, an acoustic wave with an adjustable wave characteristic. The acoustic wave characteristic may be chosen such that a resulting distortion in the wave characteristic of the probe beam compensates for the wave characteristic distortion caused by the scanning motion of the probe beam across the manufactured object.

Alternatively, the apparatus may be used by directing the pump beam of a two-wave mixing interferometer toward the acousto-optic cell 114. In a similar manner, the wave characteristic may be distorted to compensate for the wave characteristic distortion caused by the scanning motion of the probe beam across the manufactured object.

Further, the apparatus may include more than one acousto-optic cell. These acousto-optic cells may be situated in the path of one or both of the pump beam and the probe beam. These acousto-optic cells may also operate independently or in conjunction.

For example, two acousto-optic cells may be used in parallel. A probe beam and a pump beam for use by a two-wave mixing interferometer may be generated with similar frequency profiles. The probe beam of the two-wave mixing interferometer may be directed at a first acousto-optic cell. The pump beam of the two-wave mixing interferometer may be directed at the second acousto-optic cell. The first acousto-optic cell may alter the frequency profile of the probe beam by greater than 20 MHz. The second acousto-optic cell may alter the frequency profile of the pump beam by 4 MHz less than the alteration performed by first acousto-optic cell in a direction opposite to the alteration performed by the first acousto-optic cell. As such, the resulting difference in the probe beam frequency profile and that of the pump beam may be 4 MHz. If the wave characteristic distortion caused by the scanning of the probe beam across the surface of a manufactured object is a frequency shift of 4 MHz in a specific direction, the probe beam and the pump beam may be used in a two-wave mixing interferometer with less loss in sensitivity.

Figure 7:
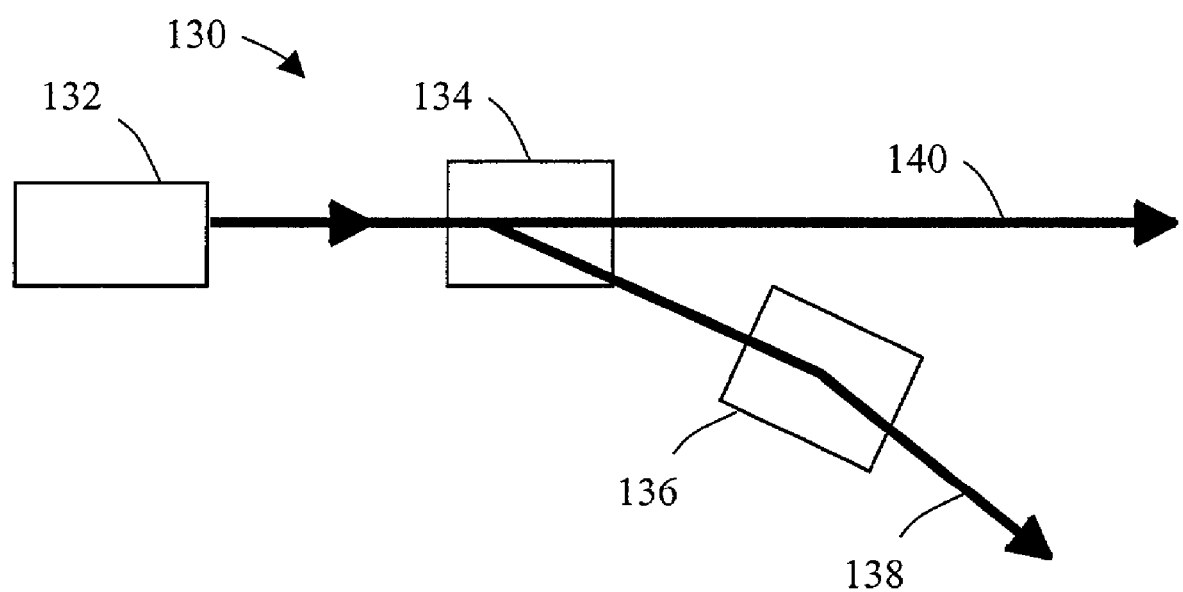
FIG. 7 is a schematic block diagram of a further apparatus for compensating for wave characteristic distortions caused by the displacements exemplified in FIG. 3 for use in the testing process of FIG. 1.

In another example, two acousto-optic cells may be used in series. FIG. 7 is a schematic block diagram of a further apparatus for compensating for wave characteristic distortions caused by the displacements exemplified in FIG. 3 for use in the testing process of FIG. 1. In this exemplary embodiment 130, the coherent electromagnetic energy generator 132, such as a laser generator, directs a generated beam of coherent electromagnetic energy toward a first acousto-optic cell 134. The first acousto-optic cell 134 may alter the wave characteristic of the generated beam. The beam of coherent electromagnetic energy with the altered wave characteristic may be directed toward a second acousto-optic cell 136. The second acousto-optic cell 136 may alter the wave characteristic of the beam of coherent electromagnetic energy again.

In such a manner, a beam of coherent electromagnetic energy may be produced which compensates for the wave characteristic distortion caused by the scanning motion of a probe beam of a two-wave mixing interferometer across a manufactured object. Either or both of the pump beam and the probe beam of a two-wave mixing interferometer may be directed through an apparatus similar to the one shown in FIG. 7.

In a typical mode of operation, a frequency distortion caused by the scanning of the probe beam across the surface of a manufactured object may be on the order of 4 MHz. The first acousto-optic cell 134 may alter the frequency by more than 20 MHz. The second acousto-optic cell 136 may alter the frequency by an amount 4 MHz less than the first acousto-optic cell 134 in a direction opposite to the alteration performed by the first acousto-optic cell 134. As such, the resulting change in a beam of coherent electromagnetic energy would be 4 MHz.

This change may be performed on either the probe beam or the pump beam of a two-wave mixing interferometer. For example, the wave characteristic adjusting device may be placed in the path of the probe beam. The wave characteristic adjusting device may also be situated in the path of the pump beam.

The acousto-optic cells, 134 and 136, may take many forms. These forms may include forms in which a piezo-electric transducer induces acoustic waves in the acousto-optic cells, 134 and 136, among others. The acousto-optic cells, 134 and 136, may be made from fused silica, gallium arsenide, gallium phosphide, germanium, lead molybdate, tellurium dioxide, lithium niobate, or any other material useful for altering electromagnetic wave characteristics with acoustic waves.

Figure 8:
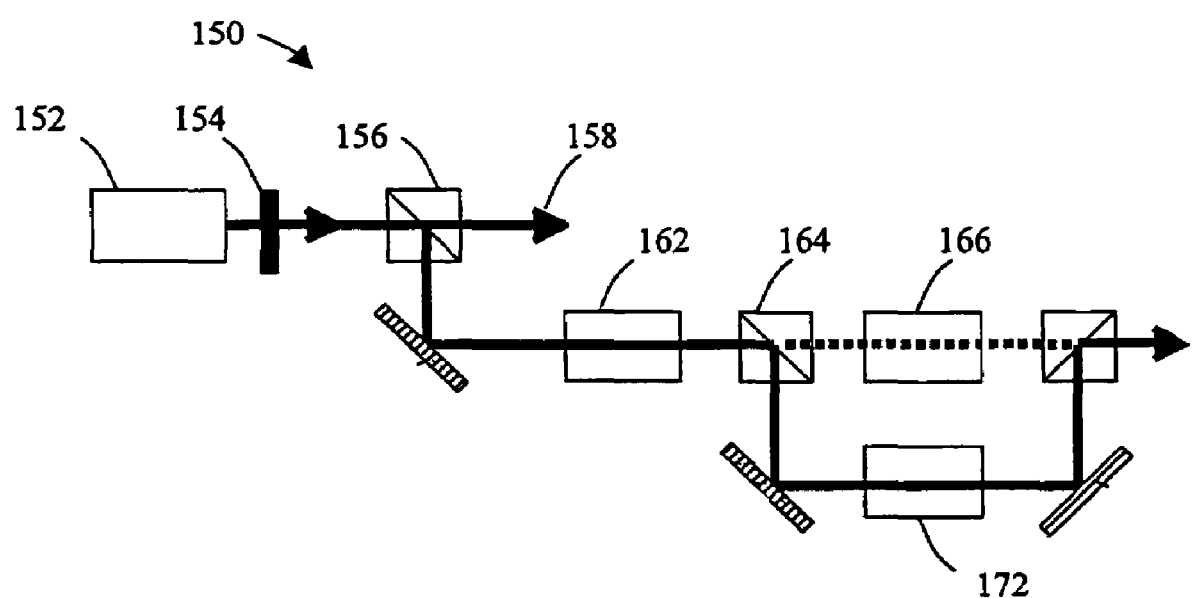
FIG. 8 is a schematic block diagram of another apparatus for compensating for wave characteristic distortions caused by the displacements exemplified in FIG. 3 for use in the testing process of FIG. 1.

FIG. 8 is a schematic block diagram of another apparatus for compensating for wave characteristic distortions caused by the displacements exemplified in FIG. 3 for use in the testing process of FIG. 1. In this exemplary apparatus 150, a coherent electromagnetic energy generator 152, such as a laser generator, directs a generated beam of coherent electromagnetic energy through a half wave plate 154. Then, the generated beam is split by a beam splitter 156. This results in a first test beam 158 and a second test beam.

The second test beam is directed to an electro-optic polarizer 162. If the electro-optic polarizer 162 operates in a first mode, the second test beam passes through a polarized beam splitter 164 to a first electro-optic phase modulator 166. If the electro-optic polarizer 162 operates in a second mode, the second test beam is deflected by a polarized beam splitter 164 to a second electro-optic phase modulator 172.

The apparatus 150 operates by alternating between the two electro-optic phase modulators 166 and 172. When the second test beam passes through either electro-optic phase modulator, the corresponding phase modulator continuously changes the phase with a slope associated with the required frequency shift. When the maximum phase for the phase modulator is reached, the electro optic polarizer switches the polarization so that the beam passes to the other electro-optic phase modulator. The other phase modulator now continuously changes the phase of the beam. Although not shown in FIG. 8, the optical paths of the two modes may have very similar lengths.

Figure 9:
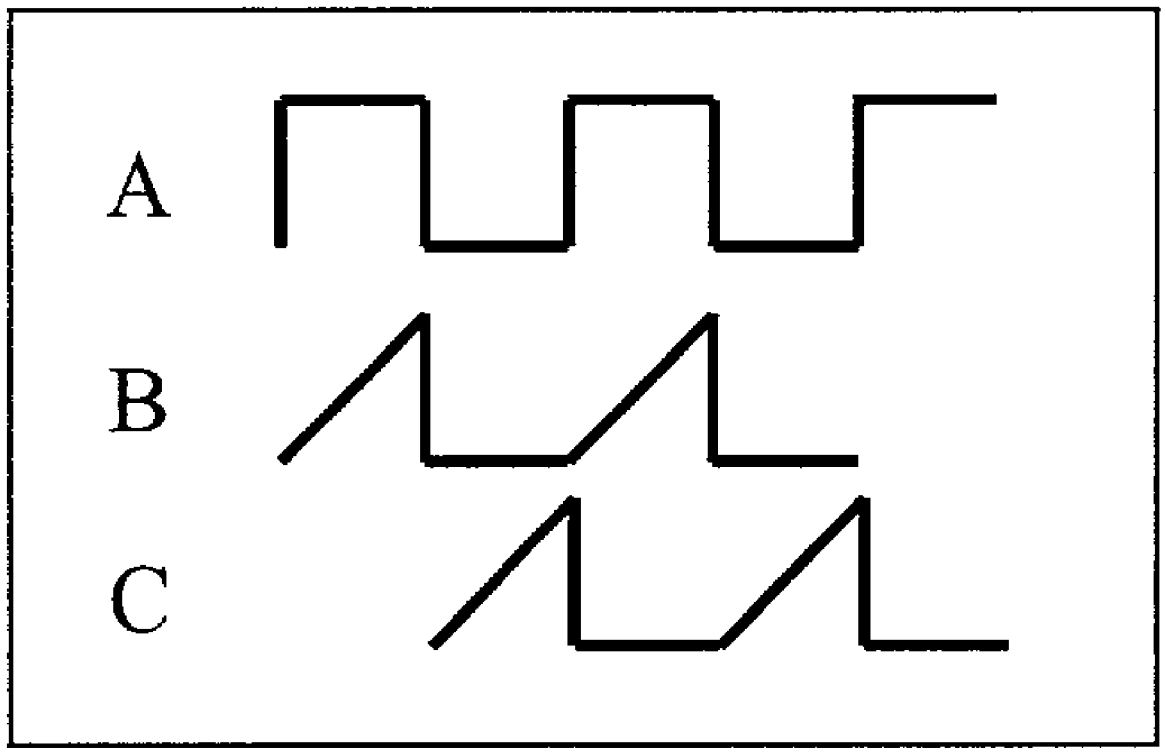
FIG. 9 is a time series graph of an exemplary operation of the apparatus of FIG. 8.

Synchronization between the three cells is important. FIG. 9 is a graph of an exemplary wave form resulting from the apparatus of FIG. 8. Line A represents a time series of the mode of the electro-optic polarizer of FIG. 8. If the mode changes to the first mode, depicted as a step up, the second test beam is directed to the first electro-optic phase modulator 166. The phase of the second test beam of coherent electromagnetic energy is altered as seen in the slope of Line B. However, the first electro-optic phase modulator 166 may reach a limit beyond which it may not alter the phase anymore.

On or before the limit of the first electro-optic phase modulator 166 is reached, the electro-optic polarizer 162 may change to the second mode as depicted by a step down of Line A in FIG. 9. The second test beam of coherent electromagnetic energy is directed to the second electro-optic phase modulator 172. The second electro-optic phase modulator 172 alters the phase as seen in Line C of FIG. 9. When the second electro-optic phase modulator 172 reaches a limit, the polarizer 162 returns to the first mode and directs the beam to the first phase modulator 166.

In this manner, a frequency shift may be achieved which compensates for a frequency shift caused by a scanning motion of a probe beam of coherent electromagnetic energy of a two-wave mixing interferometer across a manufactured object. By continuously adjusting the phase, an apparent frequency adjustment is created.

The first test beam of coherent electromagnetic energy may either be the probe beam or the pump beam of the two-wave mixing interferometer. The second test beam of coherent electromagnetic energy may be either the probe beam or the pump beam of the two-wave mixing interferometer.

Several devices may be used to generate the beam of coherent electromagnetic energy. These devices may include any device suitable for generating a beam of coherent electromagnetic energy for use in a two-wave mixing interferometer. These devices are selected from, but not limited to, a Nd:YAG laser, a Yb:YAG laser, a Nd:YVO$_4$ laser, a Nd:YLF laser, a Tm:YLF laser, a Ho:YLF laser, a Ho:YAG laser or any other device that can produce electromagnetic coherent energy like, but not limited to, an optical parametric oscillator or a harmonic generator, among others.

The system above may be augmented by placing more than one phase modulator in parallel and series. For example, three electro-optic phase modulators may be placed in parallel. The second test beam may be directed to these phase modulators by, for example, a polarizer with variable modes of operation or by a series or array of more than one polarizer.

Electro-optic phase modulators may be made from many materials. These materials may include ammonium dihydrogen phosphate, potassium dihydrogen phosphate, potassium dideuterium phosphate, lithium niobate, lithium tantalite, cadmium telluride, and any other material suitable for altering an electromagnetic wave characteristic using electrical signals.

Figure 10:
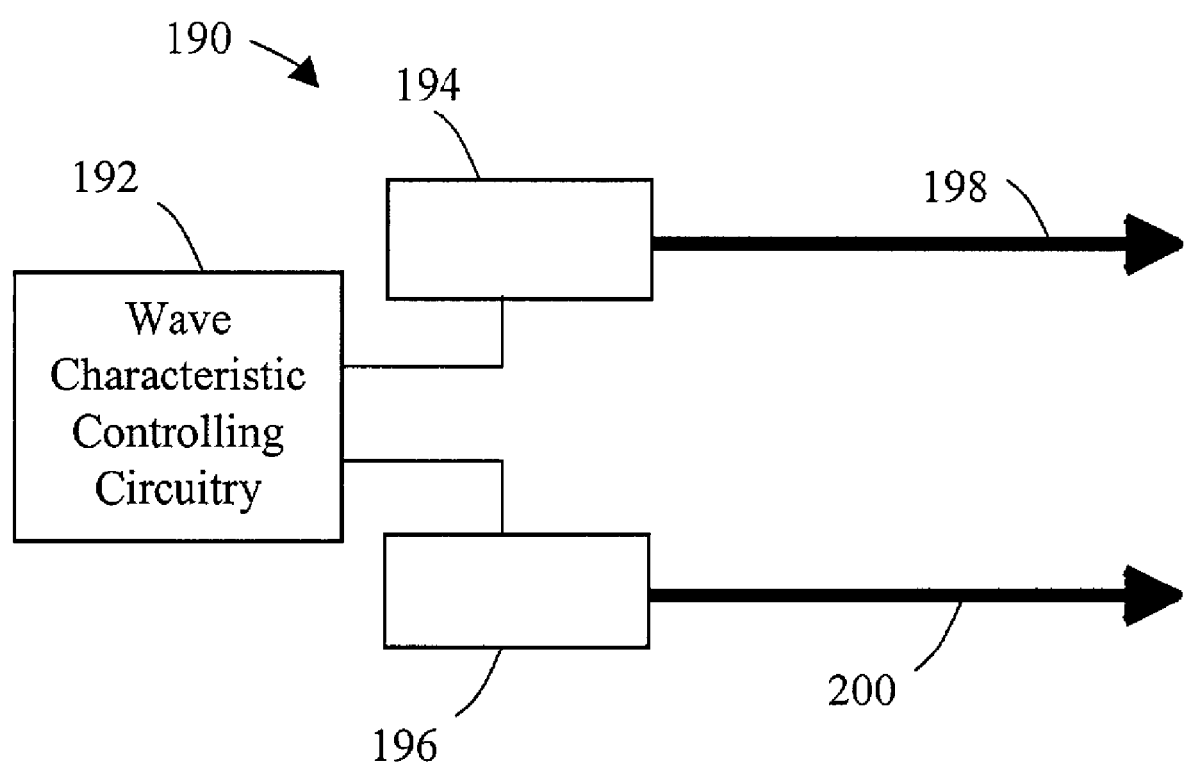
FIG. 10 is another schematic block diagram of an apparatus for apparatus for compensating for wave characteristic distortions caused by the displacements exemplified in FIG. 3 for use in the testing process of FIG. 1.

FIG. 10 is another schematic block diagram of another exemplary apparatus for compensating for wave characteristic distortions caused by the displacements exemplified in FIG. 3 for use in the testing process of FIG. 1. In the system 190 of FIG. 10, two coherent electromagnetic energy generators, 194 and 196, generate the probe beam of coherent electromagnetic energy 198 and the pump beam of coherent electromagnetic energy 200 for use in a two-wave mixing interferometer.

An wave characteristic controlling circuitry 192, may be used to alter the frequency of the probe beam 198, the pump beam 200, or both, to compensate for the scanning motion of the probe beam across the surface of the manufactured object. For example, the optical frequency controller 192 may manipulate an electro-optic phase modulator associated with one of the coherent electromagnetic energy generators.

In addition, the wave characteristics of the probe beam 198 and/or the pump beam 200 may be altered by the apparatuses described above. For example, the probe beam 198 and/or the pump beam 200 may be directed through any of the apparatuses depicted in FIG. 5, 6, 7, or 8.

In addition, the optical frequencies of the electromagnetic energy generator 194 or 196, or both generators 194 and 196 may be individually controlled by a fast frequency tuning device in order to produce an optical frequency difference between the two beams 198 and 200 that corresponds to the frequency shift that compensates for the normal or apparent normal displacement.

As an example, the two electromagnetic energy generators might be two nonplanar-ring-oscillators as manufactured by LightWave Electronics located in Mountain View, Calif. and equipped with a fast piezoelectric frequency tuning as described in U.S. Pat. No. 4,829,532.

Several devices may be used to generate the beam of coherent electromagnetic energy. These devices may include any device suitable for generating a beam of coherent electromagnetic energy for use in a two-wave mixing interferometer. These devices are selected from, but not limited to, a Nd:YAG laser, a Yb:YAG laser, a Nd:YVO$_4$ laser, a Nd:YLF laser, a Tm:YLF laser, a Ho:YLF laser, a Ho:YAG laser or any other device that can produce electromagnetic coherent energy like, but not limited to, an optical parametric oscillator or a harmonic generator, among others.

Figure 11:
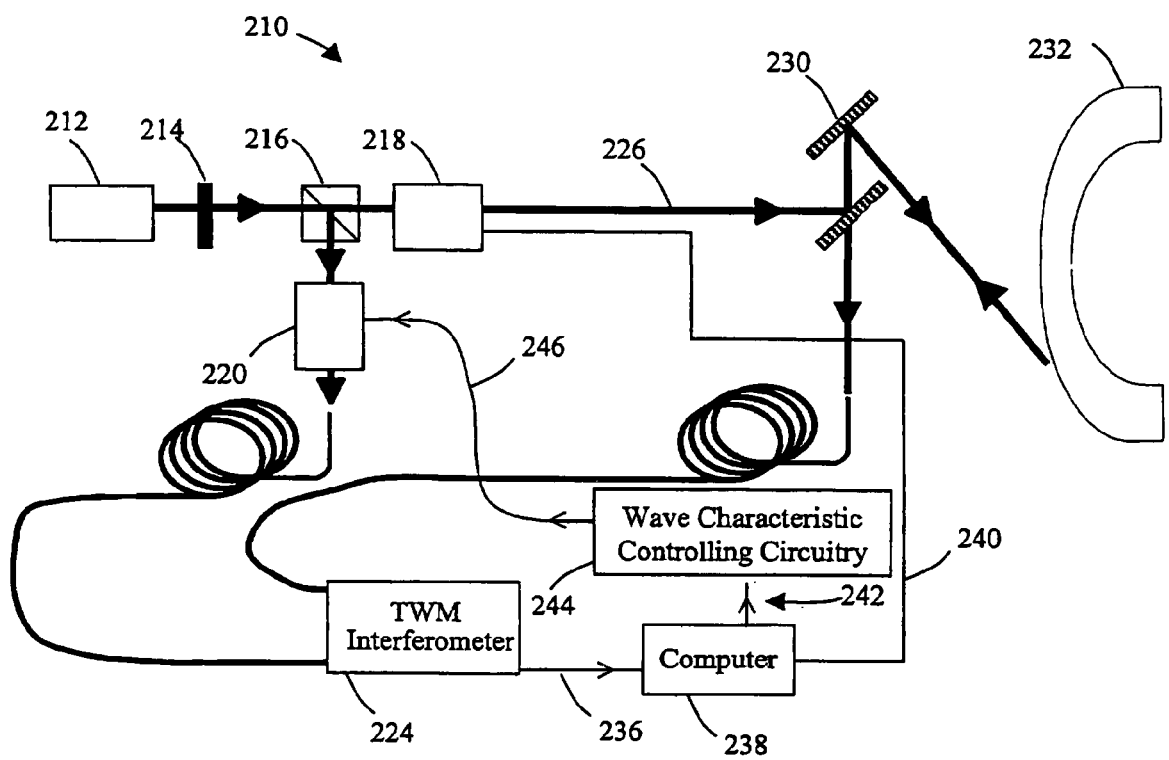
FIG. 11 is a schematic block diagram of a system for compensating for wave characteristic distortions caused by the displacements exemplified in FIG. 3 for use in the testing process of FIG. 1.

FIG. 11 is a schematic block diagram of an exemplary system for compensating for wave characteristic distortions caused by the displacements exemplified in FIG. 3 for use in the testing process of FIG. 1. In the exemplary system 210, a coherent electromagnetic energy generator generates a generated beam of coherent electromagnetic energy. The generated beam of coherent electromagnetic energy is split by a beam splitter 216 into a probe beam and a pump beam. The pump beam is directed through a wave characteristic adjusting device 220. Then the pump beam is directed to a two-wave mixing interferometer 224.

In one embodiment, the probe beam may pass through a synthetic signal generator 218. The synthetic signal generator may add an additional wave characteristic to the probe beam. The resulting beam 226 is scanned across a manufactured object 232 using a scanning mirror 230. The resulting beam 226 reflects from the manufactured object with an altered wave characteristic. The altered wave characteristic may have components indicative of both a sonic energy signal and the scanning motion of the resulting beam 226.

The resulting beam 226 is directed to the two-wave mixing interferometer 224. In the two-wave mixing interferometer the resulting beam 226 interacts with the pump beam in a photo-refractive crystal. From this interaction, a measurement may be made if the frequency of the reflected resulting beam is similar to the frequency of the pump beam 222.

A wave characteristic controlling system may be coupled to the two-wave mixing interferometer 224 through a link 236. The two-wave mixing interferometer 224 may communicate information indicative of the sensitivity of the measurement. The wave characteristic controlling system may determine the wave characteristic adjustment required to compensate for the scanning motion of the beam 226.

As shown in this exemplary embodiment, the wave characteristic controlling system may be a computer 238 with a wave characteristic controller 244. The computer 238 may communicate with the wave characteristic controller 244 through a link 242. The wave characteristic controller 244 may direct the wave characteristic adjusting device 220 through a link 246.

The computer may also communicate with the synthetic signal generator through a link 240. The computer may direct the synthetic signal generator to produce a specific synthetic signal. Also, the synthetic signal generator may communicate information associated with the specific synthetic signal which has been generated with the computer. The computer 238 may use the synthetic signal measured by the two-wave mixing interferometer 224 as feedback information to adjust the wave characteristic adjustment produced by wave characteristic device 220. In one exemplary embodiment, the amplitude and/or phase of the measured synthetic signal are compared to the amplitude and/or phase of the synthetic signal generated by the computer 238 and the synthetic signal generator 218. The wave characteristic shift produced by the wave characteristic device 220 through the link 246 is changed to make the amplitude and/or phase of the measured synthetic signal approximate the amplitude and/or phase of the generated synthetic signal. The computer may obtain information about the synthetic signal from the synthetic signal generator or from a-priori knowledge of the parameters of the synthetic signal. The computer uses the comparison to determine the wave characteristic adjustment compensating for the scanning motion of the beam 226 or other normal movements. The compensatory wave characteristic adjustment may be produced by wave characteristic device 220.

For example, the synthetic signal may have a known frequency, amplitude and phase which can be compared to the signal after reflection from the manufactured object. This synthetic signal should not interfere with the ultrasonic signal so it must be confined, in time or in frequency, in a domain not used by the ultrasonic signal. For example, the synthetic signal might be a single frequency oscillation at 15 MHz whereas the ultrasonic signal of interest in the frequency range of 1-5 MHz, or it might be a single pulse or a short series of pulse occurring before the ultrasonic signal. An electro-optic phase modulator can be used to induce such a synthetic signal. The reflected beam may be demodulated by the two-wave mixing interferometer and the synthetic signal may be isolated from the ultrasonic signal. In the present example, the synthetic signal is filtered out from the measured signal and the amplitude of the signal at 15 MHz is maximized by adjusting the wave characteristic device. In the case where a single pulse or a short series of pulses were used, the amplitude and phase of the measured synthetic signal could be compared to the amplitude and phase of the synthetic signal generated by the computer 238 and the synthetic signal generator 218. Then, the wave characteristic shift produced by the wave characteristic device 220 through the link 246 is changed to make the phase and amplitude of the measured synthetic signal match the amplitude and phase of the generated synthetic signal.

The synthetic signal generator may take several forms. These forms may include an electro-optic phase modulator, an acousto-optic cell, a magnetic cell, or a mechanical phase modulating device.

The computer may use information from and about the two-wave mixing interferometer to determine the wave characteristic adjustment required to compensate for the scanning motion of the beam 226. Further, the computer may use information about the object 232, a sonic energy signal associated with the manufactured object 232, and the generated beam of coherent electromagnetic energy, among others.

In another example, the synthetic signal generator 218 may be incorporated in the coherent electromagnetic energy generator 212. Further, the coherent electromagnetic energy generator 212 may generate a characteristic signal which replaces the synthetic signal.

The beams may be directed to the various elements through several means. These means include mirrors, beam splitters and fiber optical cables, among others.

The coherent electromagnetic energy generator 212 may be one of several devices. These devices may include any device suitable for generating a beam of coherent electromagnetic energy for use in a two-wave mixing interferometer. These devices are selected from, but not limited to, a Nd:YAG laser, a Yb:YAG laser, a Nd:YVO$_4$ laser, a Nd:YLF laser, a Tm:YLF laser, a Ho:YLF laser, a Ho:YAG laser or any other device that can produce electromagnetic coherent energy like, but not limited to, an optical parametric oscillator or a harmonic generator, among others.

The coherent electromagnetic energy generator 212 may also be more than one device. The probe beam and the pump beam may be generated by separate coherent electromagnetic energy generators.

Figure 12:
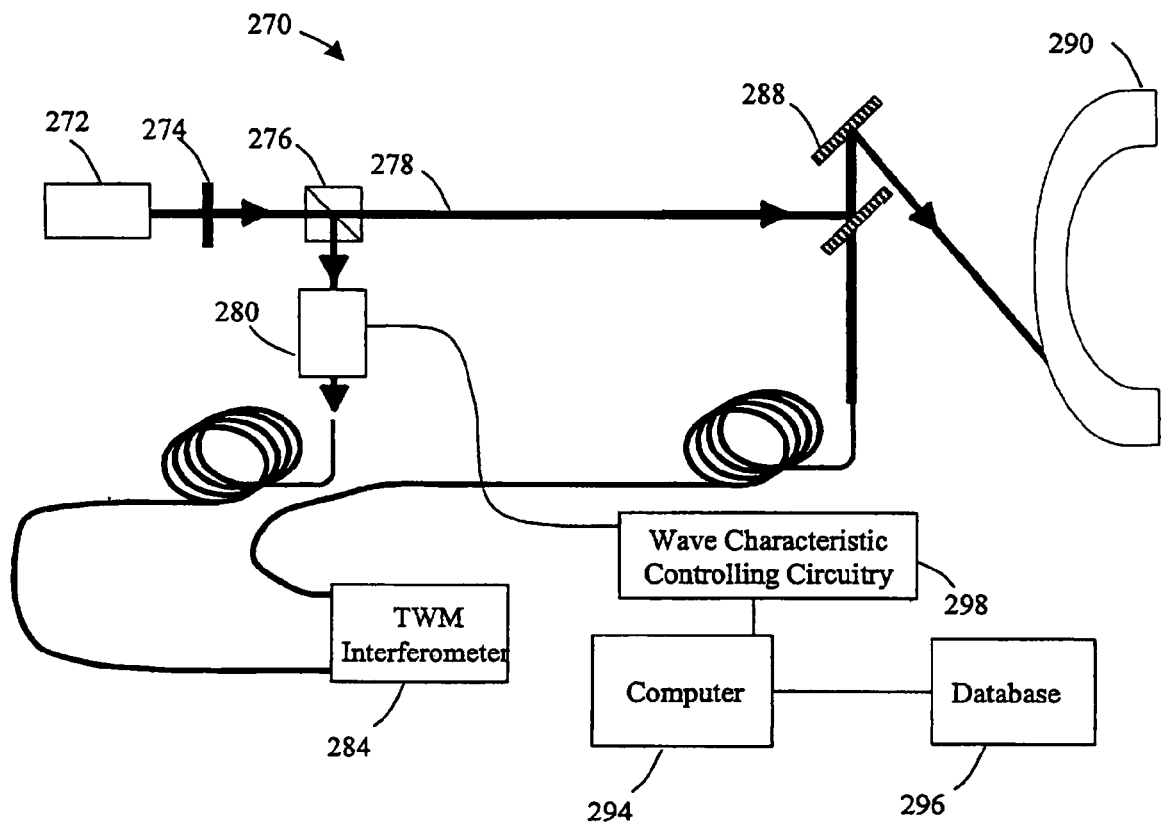
FIG. 12 is a schematic block diagram of a system for compensating for wave characteristic distortions caused by the displacements exemplified in FIG. 3 for use in the testing process of FIG. 1.

FIG. 12 is schematic block diagram of another exemplary system for compensating for wave characteristic distortions caused by the displacements exemplified in FIG. 3 for use in the testing process of FIG. 1. The system 270 has a coherent electromagnetic energy generator 272, a two-wave mixing interferometer 284, and a wave characteristic controlling system.

In this exemplary embodiment, the coherent electromagnetic energy generator 272 generates a beam of coherent electromagnetic energy. The beam of coherent electromagnetic energy may be split into a probe beam 278 and a pump beam. The probe beam 278 may be scanned across the surface of a manufactured object 290. The probe beam may reflect from the surface and be directed to the two-wave mixing interferometer 284.

The pump beam may be directed through a wave characteristic adjusting device 280 to the two-wave mixing interferometer 284. A wave characteristic controlling system may direct the wave characteristic adjusting device 280 to adjust the wave characteristics of the pump beam.

In FIG. 12, the wave characteristic adjusting device 280 is depicted as being situated in the path of the pump beam. However, the wave characteristic adjusting device 280 may also be placed in the path of the probe beam.

The wave characteristic adjusting device 280 may take many forms. These forms may include the apparatuses described in FIGS. 5, 6, 7, and 8. The forms may also include any device which effectively alters the wave characteristics of a beam of coherent electromagnetic energy.

The beams may be directed using several devices. These devices may include mirrors, fiber optic cables, and beam splitters, among others.

In this exemplary embodiment, the wave characteristic controlling system has a computer 294, a database 296, and a wave characteristic controlling circuitry 298. The computer 294 may direct the wave characteristic controlling circuitry 298 to direct the operation of the wave characteristic adjusting device 280.

The database 296 may take many forms. These forms may include a readable medium within the computer, an external hard drive, a networked storage device, and others. The database may hold data of an expected result, data associated with the object shape, or parameters associated with the object, the beams, and two-wave mixing interferometer 284, among others. Further, the computer may use the database to determine the controlling action of the wave characteristic controlling circuitry 298.

The wave characteristic controlling system may include all, some, or none of the computer 294, the wave characteristic controlling circuitry 298 and the database 296. Further, the two-wave mixing interferometer 284 may be connected to the wave characteristic controlling system. The wave characteristic controlling system may use the output from the two-wave mixing interferometer 284 to determine the behavior of the wave characteristic adjusting device 280.

The computer 294, the wave characteristic controlling circuitry 298, and the database 296 may be encompassed in one device, separately, or in any combination. The computer may take many forms. These forms may include a networked computer, a handheld device, and any system with a microprocessor, among others.

The coherent electromagnetic energy generator 272 may be one of several devices. These devices may include any device suitable for generating a beam of coherent electromagnetic energy for use in a two-wave mixing interferometer. These devices are selected from, but not limited to, a Nd:YAG laser, a Yb:YAG laser, a Nd:YVO$_4$ laser, a Nd:YLF laser, a Tm:YLF laser, a Ho:YLF laser, a Ho:YAG laser or any other device that can produce electromagnetic coherent energy like, but not limited to, an optical parametric oscillator or a harmonic generator, among others.

The coherent electromagnetic energy generator 272 may also be more than one device. The probe beam and the pump beam may be generated by separate coherent electromagnetic energy generators.

Figure 13:
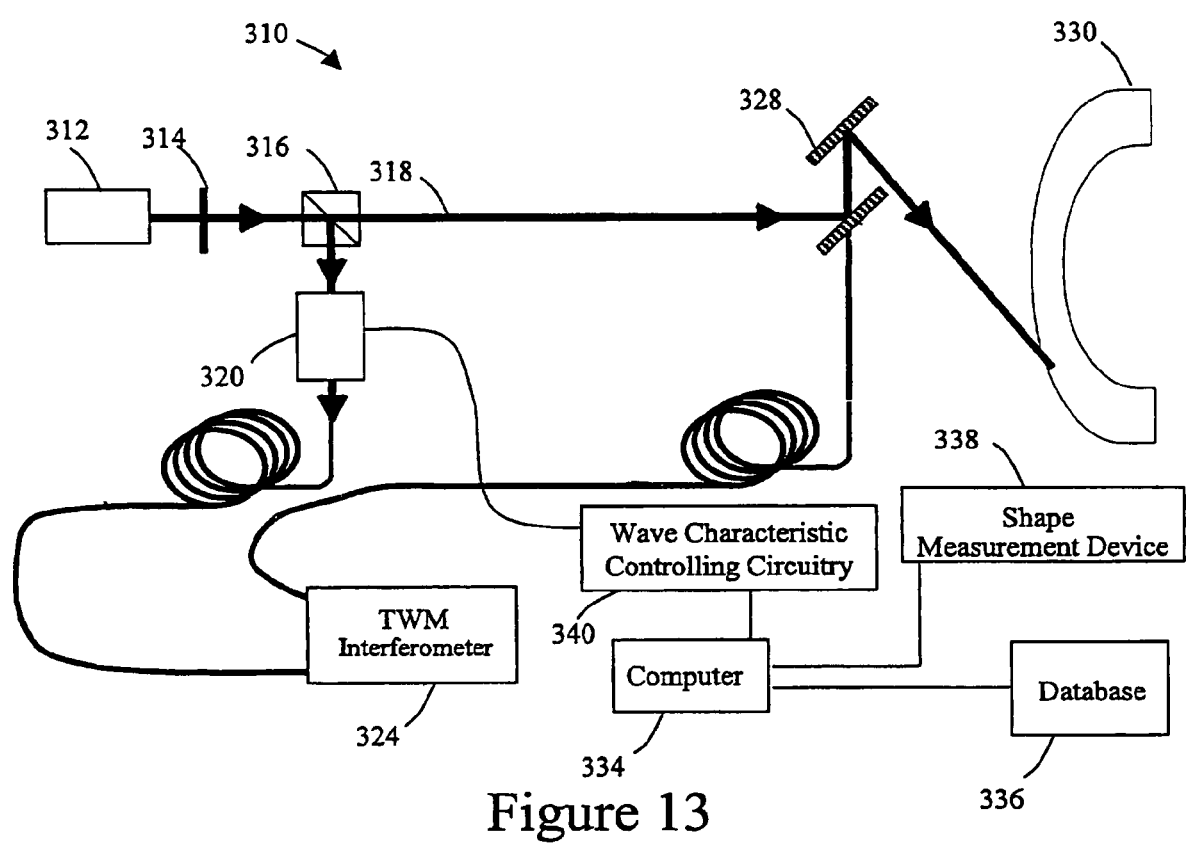
FIG. 13 is another schematic block diagram of another system for compensating for wave characteristic distortions caused by the displacements exemplified in FIG. 3 for use in the testing process of FIG. 1.

FIG. 13 is another schematic block diagram of another system for compensating for wave characteristic distortions caused by the displacements exemplified in FIG. 3 for use in the testing process of FIG. 1. In a process similar to that of FIG. 12, a coherent electromagnetic energy generator 312 generates a generated beam of coherent electromagnetic energy. The beam may be split into a pump beam and a probe beam 318 by a beam splitter 316. The pump beam may be directed through a wave characteristic adjusting device 320 to a two-wave mixing interferometer 324.

The probe beam 318 may be scanned across a manufactured object 330. The probe beam may be directed by a scanning mirror 328. The probe beam may reflect from the manufactured object 330 and be directed to a two-wave mixing interferometer 324.

The beams may be directed using several devices. These devices may include mirrors, fiber optic cables, and beam splitters, among others.

The wave characteristic adjusting device 320 is depicted as being situated in the path of the pump beam. However, it may also be placed in the path of the probe beam. Additionally, more than one wave characteristic adjusting device may be placed in either or both of the paths of the pump beam and the probe beam.

The wave characteristic adjusting device 320 may take many forms. These forms may include the apparatuses described in FIGS. 5, 6, 7, and 8. The forms may also include any device which effectively alters the wave characteristics of a beam of coherent electromagnetic energy.

A wave characteristic controlling system may direct the actions of the wave characteristic adjusting device 320. Although not depicted as such, the wave characteristic controlling system may be coupled to the two-wave mixing interferometer 324. The wave characteristic controlling system may use the output from the two-wave mixing interferometer 324 to determine the actions of the wave characteristic adjusting device 320. The wave characteristic controlling system may also direct the performance of the two-wave mixing interferometer 324. For example, a photo-refractive crystal in the two-wave mixing interferometer 324 may utilize a voltage. The voltage may be controlled by the wave characteristic controlling system.

In this exemplary embodiment, the wave characteristic controlling system has a computer 334, a database 336, a shape measurement device 338, and a wave characteristic controlling circuitry 340. The computer 334 may direct the wave characteristic controlling circuitry 340 to direct the operation of the wave characteristic adjusting device 320.

The database 336 may take many forms. These forms may include a readable medium within the computer, an external hard drive, a networked storage device, and others. The database may hold data of an expected result, data associated with the object shape, or parameters associated with the object, the beams, and two-wave mixing interferometer 324, among others. Further, the computer may use the database to determine the controlling action of the wave characteristic controlling circuitry 340.

The shape measurement device may take many forms. These forms may include any optical, acoustic, or other device capable of measuring the shape of the objected 330. In addition, the computer 334 may determine the actions of the wave characteristic adjusting device 320 from the measurements of the shape measurement device 338.

The computer 334 may take many forms. These forms may include a networked computer, a handheld device, and any system with a microprocessor, among others.

The wave characteristic controlling system may include all, some, or none of the computer 334, the wave characteristic controlling circuitry 340, the shape measurement device 338, and the database 336. The computer 334, the wave characteristic controlling circuitry 340, the shape measurement device 338 and the database 336 may be encompassed in one device, separately, or in any combination.

Figure 14:
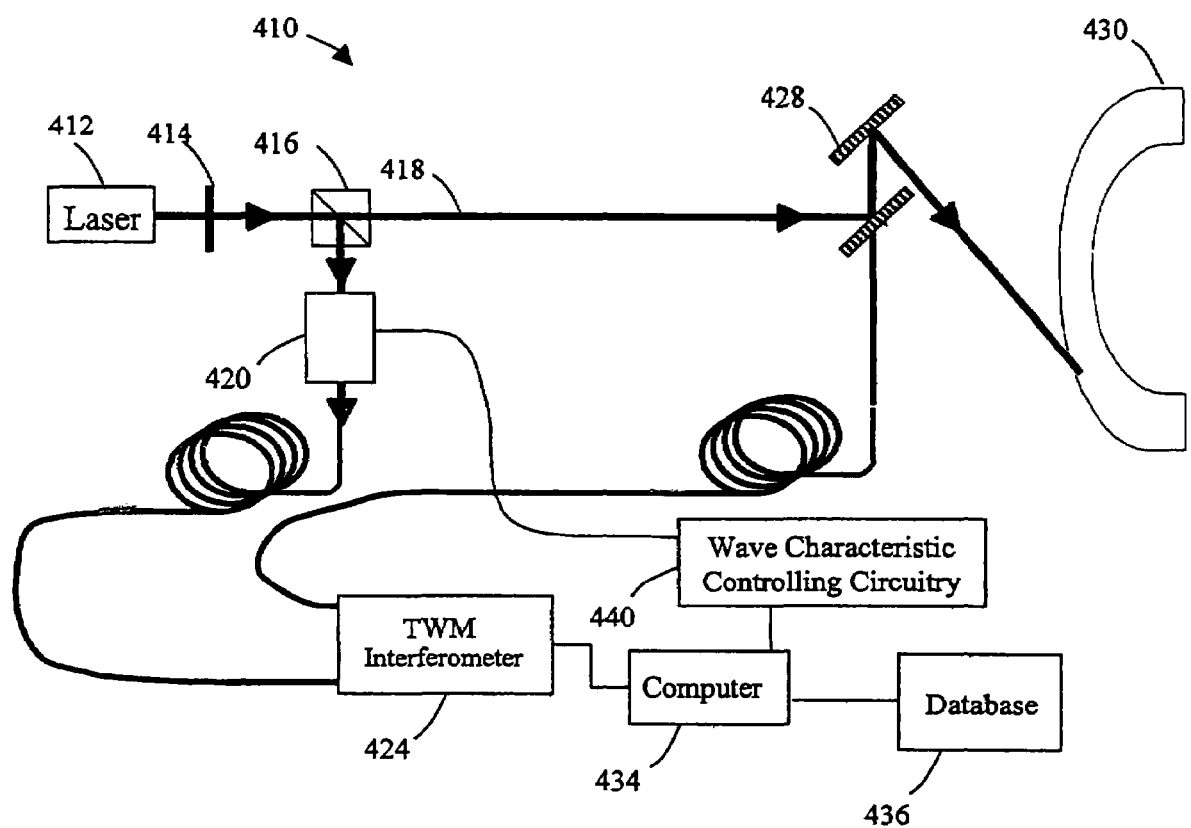
FIG. 14 is a further schematic block diagram of a system for compensating for wave characteristic distortions caused by the displacements exemplified in FIG. 3 for use in the testing process of FIG. 1.

FIG. 14 is a further schematic block diagram of a system for compensating for wave characteristic distortions caused by the displacements exemplified in FIG. 3 for use in the testing process of FIG. 1. In a process similar to that of FIG. 12, a coherent electromagnetic energy generator 412 generates a generated beam of coherent electromagnetic energy. The beam may be split into a pump beam and a probe beam 418 by a beam splitter 416. The pump beam may be directed through a wave characteristic adjusting device 420 to a two-wave mixing interferometer 424.

The probe beam 418 may be scanned across a manufactured object 430. The probe beam may be directed by a scanning mirror 428. The probe beam may reflect from the manufactured object 430 and be directed to a two-wave mixing interferometer 424.

The beams may be directed using several devices. These devices may include mirrors, fiber optic cables, and beam splitters, among others.

The wave characteristic adjusting device 420 is depicted as being situated in the path of the pump beam. However, it may also be placed in the path of the probe beam. Additionally, more than one wave characteristic adjusting device may be placed in either or both of the paths of the pump beam and the probe beam.

The wave characteristic adjusting device 420 may take many forms. These forms may include the apparatuses described in FIGS. 5, 6, 7, and 8. The forms may also include any device which effectively alters the wave characteristics of a beam of coherent electromagnetic energy.

A wave characteristic controlling system may direct the actions of the wave characteristic adjusting device 420. The wave characteristic controlling system may use the output from the two-wave mixing interferometer 424 to determine the actions of the wave characteristic adjusting device 420. The wave characteristic controlling system may also direct the performance of the two-wave mixing interferometer 424. For example, a photo-refractive crystal in the two-wave mixing interferometer 424 may utilize a voltage. The voltage may be controlled by the wave characteristic controlling system.

In addition, the wave characteristic controlling system may be coupled with a scanning system. The wave characteristic controlling system may interact with the scanning system to determine the actions of the wave characteristic adjusting device 420. The wave characteristic controlling system may also participate in directing the scanning system. Further, the wave characteristic controlling system may be coupled to a testing system such as a laser ultrasound testing system. The wave characteristic controlling system may determine the actions of the wave characteristic adjusting device 420 from interactions with the testing system.

In this exemplary embodiment, the wave characteristic controlling system has a computer 434, a database 436, and a wave characteristic controlling circuitry 440. The computer 434 may direct the wave characteristic controlling circuitry 440 to direct the operation of the wave characteristic adjusting device 420.

The database 436 may take many forms. These forms may include a readable medium within the computer, an external hard drive, a networked storage device, and others. The database may hold data of an expected result, data associated with the object shape, or parameters associated with the object, the beams, and two-wave mixing interferometer 424, among others. Further, the computer may use the database to determine the controlling action of the wave characteristic controlling circuitry 440.

The computer may take many forms. These forms may include a networked computer, a handheld device, and any system with a microprocessor, among others.

The wave characteristic controlling system may include all, some, or none of the computer 434, the wave characteristic controlling circuitry 440, and the database 436. The computer 434, the wave characteristic controlling circuitry 440, the shape measurement device 438 and the database 436 may be encompassed in one device, separately, or in any combination.

Figure 15:
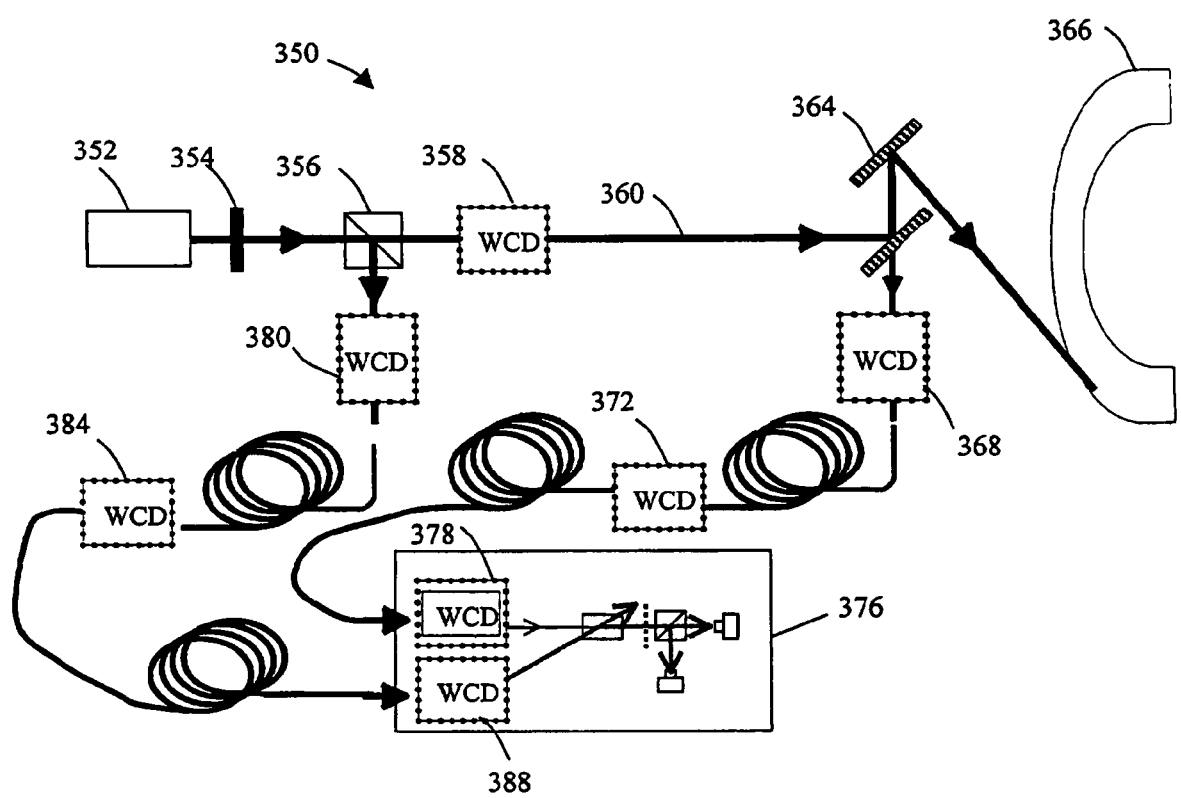
FIG. 15 is a schematic block diagram indicating a plurality of possible locations for the apparatuses exemplified in FIGS. 5, 6, 7, and 8.

FIG. 15 is a schematic block diagram indicating a plurality of possible locations for the apparatuses exemplified in FIGS. 5, 6, 7, and 8. A wave characteristic adjusting device may be placed in one, each or any combination of locations in the system 350. For example, a wave characteristic adjusting device 358 may be place in the path of the probe beam 360 before it is scanned across the manufactured object 366.

A wave characteristic adjusting device 368 may be placed after the probe beam reflects from the surface of the manufactured object 366. Further, a wave characteristic adjusting device 372 may be placed in the path of the probe beam as the probe beam is directed to a two-wave mixing interferometer 376. The wave characteristic adjusting device 372 may, for example, be placed between two fiber optic cables 370 and 374.

A wave characteristic adjusting device 380 may be placed in the path of the pump beam. Further, a wave characteristic adjusting device 384 may be placed between two fiber optic cables, 382 and 386, carrying the pump beam to a two-wave mixing interferometer 376.

A wave characteristic adjusting device 378 may be placed internal to the two-wave mixing interferometer 376 in the path of the probe beam. Furthermore, a wave characteristic adjusting device 388 may be situated internal to the two-wave mixing interferometer 376 in the path of the pump beam.

The wave characteristic adjusting devices above may take many forms. These forms may include those apparatuses depicted in FIGS. 5, 6, 7, and 8. The wave characteristic adjusting devices may also take any form which effectively alters the wave characteristics of a beam of coherent electromagnetic energy.

The coherent electromagnetic energy generator 352 may be one of several devices. These devices may include any device suitable for generating a beam of coherent electromagnetic energy for use in a two-wave mixing interferometer. These devices are selected from, but not limited to, a Nd:YAG laser, a Yb:YAG laser, a Nd:YVO$_4$ laser, a Nd:YLF laser, a Tm:YLF laser, a Ho:YLF laser, a Ho:YAG laser or any other device that can produce electromagnetic coherent energy like, but not limited to, an optical parametric oscillator or a harmonic generator, among others.

The coherent electromagnetic energy generator 352 may also be more than one device. The probe beam and the pump beam may be generated by separate coherent electromagnetic energy generators.

Figure 16:
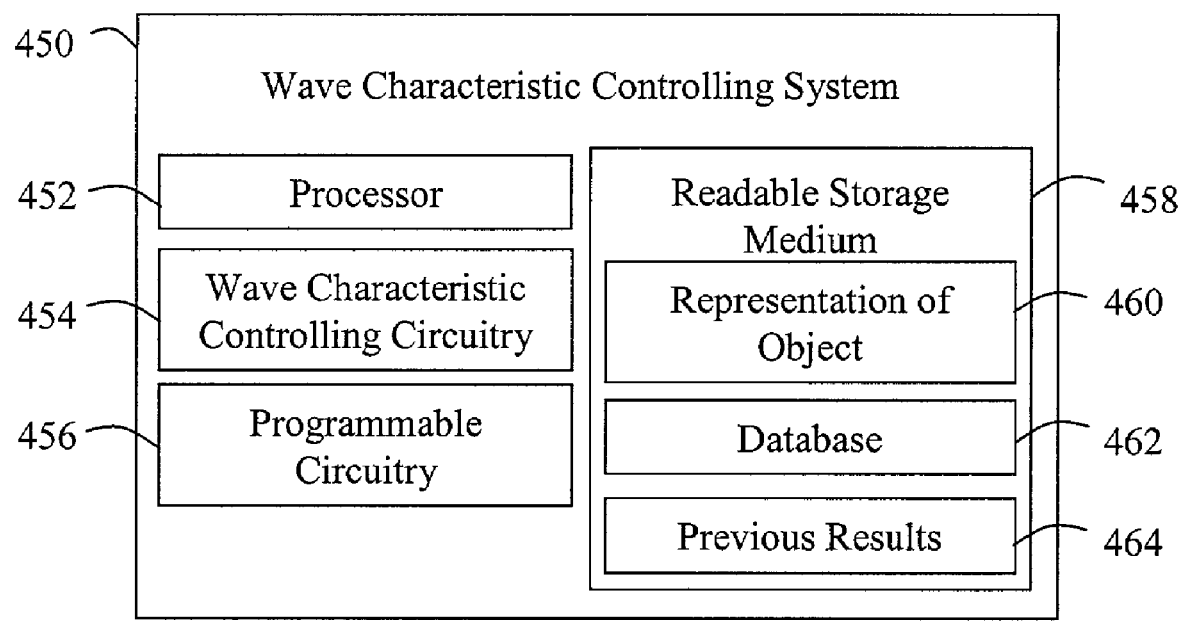
FIG. 16 is a block diagram of an apparatus for use in the systems exemplified in FIGS. 11, 12, 13, and 14.

FIG. 16 is a block diagram of an apparatus for use in the systems exemplified in FIGS. 11, 12, 13, and 14. The system 450 depicts a wave characteristic controlling system. The wave characteristic controlling system may have the functionality described above in relation to FIGS. 11, 12, 13 and 14.

The wave characteristic controlling system may have many elements. These elements may include a processor 452, a wave characteristic controlling circuitry 454, a programmable circuitry 456, and a readable storage medium 458. The wave characteristic controlling system 450 may hold all, some or none of these elements. These elements may be enclosed in one device, separately or in any configuration.

The readable storage medium 458 may hold a representation of the manufactured object 460, a database 462, and previous results 464. The readable storage medium 458 may also hold swappable programs, models and instructions for use by the processor 452, programmable circuitry 456, or wave characteristic controlling circuitry 454. The representation of the manufactured object 460 may be a computer-aided-drafting representation of the manufactured object. Further, the database 462 may hold information generated from a computer-aided-drafting representation of the manufactured object.

The wave characteristic controlling system may determine an action for one or more wave characteristic adjusting devices. The wave characteristic controlling system may be coupled to a two-wave mixing interferometer, a scanning system, a testing system, a synthetic signal generation system, a shape measurement system and a network, among others. The wave characteristic controlling system may utilize these systems and the two-wave mixing interferometer in determining the action of the one or more wave characteristic adjusting devices. The wave characteristic controlling system may also use information about the position and angle of the scanning mirror to determine the action of the wave characteristic adjusting device.

In an exemplary embodiment, the processor may use the programmable circuitry and information from the database to determine the action of the wave characteristic adjusting device. The processor may then direct the wave characteristic controlling circuitry to control the wave characteristic adjusting device.

In another embodiment, the processor may determine the action of the wave characteristic adjusting device using the programmable circuitry 456 and the representation of the manufactured object 460. Further the process may determine the action of the wave characteristic adjusting device from models such as propagation models, movement models, and shape models. These models may utilize a representation of the manufactured object 460 such as a computer-aided-drafting representation of the manufactured object. In addition, the processor may determine the actions of the wave characteristic adjusting device from previous measurements.

The wave characteristic controlling system 450 may operate using forward controlling action by predicting the wave characteristic distortion caused by the scanning motion of the probe beam. Further, the wave characteristic controlling system 450 may operate in a feedback controlling action from interactions with the two-wave mixing interferometer.

Figure 17:
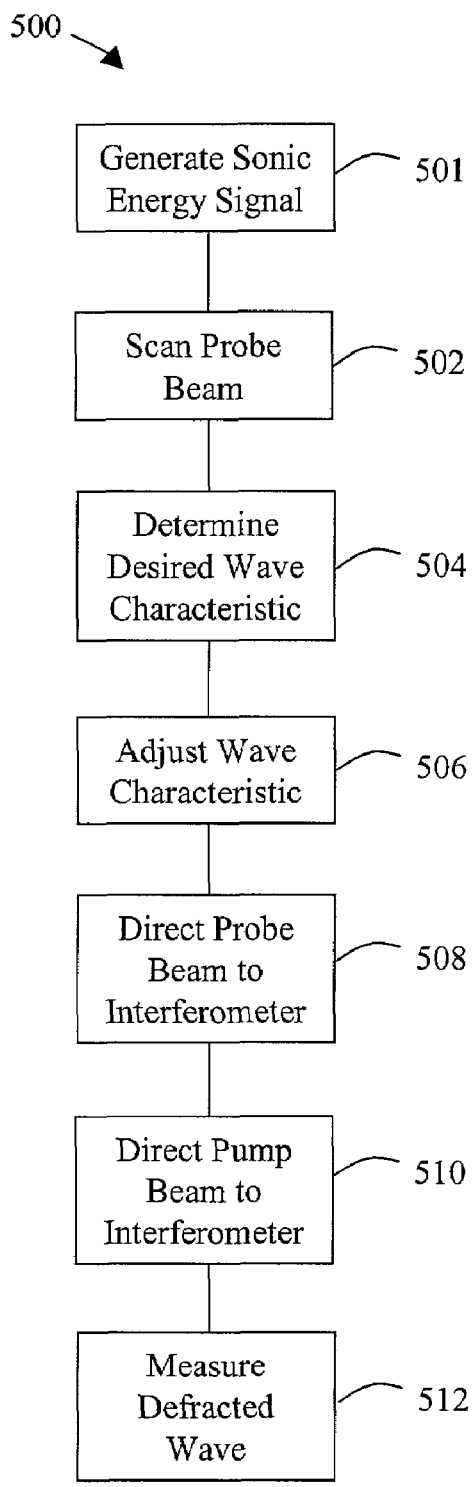
FIG. 17 is a block diagram of a method of operation for systems similar to those exemplified in FIGS. 11, 12, 13, and 14.

FIG. 17 is a block diagram of a method of operation for systems similar to those exemplified in FIGS. 11, 12, 13, and 14. In the method 500, a sonic energy signal is generated, as shown by a block 501. The sonic energy signal is then measured. The measurement of the sonic energy signal is accomplished by scanning a probe beam across the surface of a manufactured object as seen in the box 502. In a box 504, the wave characteristic controlling system may determine a desired wave characteristic for the pump beam, the probe beam or both. The desired wave characteristic may compensate for the wave characteristic distortion caused by the scanning motion of the probe beam of the two-wave mixing interferometer. The wave characteristic controlling system may predetermine the desired wave characteristic or it may determine the desired wave characteristic contemporarily to the scanning or generation.

In a next box 506, the wave characteristic of a beam is adjusted to the desired wave characteristic. This may be performed by a wave characteristic adjusting device under the direction of the wave characteristic controlling system. It may also be performed independently. The adjusted beam may be the probe beam, the pump beam or both. In a further step 508, the probe beam is directed to the two-wave mixing interferometer. In addition, the pump beam is directed to the two-wave mixing interferometer. These steps, 508 and 510, may occur simultaneously.

As a result, the pump beam and the probe beam form a diffracted beam in the two-wave mixing interferometer. In a next step 512, the diffracted beam is measured. As a consequence, a measurement is made using a two-wave mixing interferometer in a rapid scanning system.

As such, a method and apparatus for compensating for wave characteristic distortions caused by a scanning motion of a probe beam is described. In view of the above detailed description of the present invention and associated drawings, other modifications and variations will now become apparent to those skilled in the art. It should also be apparent that such other modifications and variations may be effected without departing from the spirit and scope of the present invention as set forth in the claims which follow.

What is claimed is:

1. A system for testing a physical attribute of a manufactured object, the system comprising:
    a laser ultrasound generation system;
    a beam of coherent electromagnetic energy directed from the laser ultrasound generation system;
    a beam splitter in the path of the beam of coherent electromagnetic energy;
    a two wave mixing interferometer;
    a probe beam from the beam splitter directed at the manufactured object that reflects from the manufactured object with an altered wave characteristic thereby defining a resulting beam;
    a pump beam from the beam splitter directed at a wave characteristic adjusting device having an electro-optic polarizer in communication with a portion of the pump beam, a first electro-optic phase modulator in communication with a portion of the pump beam when the electro-optic polarizer operates in a first mode, and a second electro-optic phase modulator in communication with a portion of the pump beam when the electro-optic polarizer operates in a second mode, so that when the pump beam is communicated with the at least one of the first or second electro-optic phase modulators, the pump beam is frequency adjusted;
    a two wave mixing interferometer in communication with the resulting beam and the frequency adjusted pump beam and in communication with the wave characteristic adjusting device, so that the frequency adjustment of the pump beam is based on a comparison of the pump beam and the resulting beam that compensates for altered wave characterstics used by a scanning motion of the probe beam.

2. The system of claim 1, further comprising a processor in communication with the two wave mixing interferometer and the wave characteristic adjusting device, so that when information is communicated from the two wave mixing interferometer to the processor indicative of interaction between the pump beam and the resulting beam the processor determines a wave characteristic adjustment required to compensate for the scanning motion of the beam that is communicated to the wave characteristic adjusting device.

3. The system of claim 1, wherein the resulting beam reflects from the manufactured object with an altered wave characteristic having components indicative of a sonic energy signal and the scanning motion of the resulting beam.

4. The system of claim 1, wherein the probe beam is directed at the manufactured object from a scanning mirror.

5. A wave characteristic adjusting device for adjusting a wave characteristic of a beam of coherent electromagnetic energy distorted by scanning the beam of coherent electromagnetic energy, wherein the beam of coherent electromagnetic energy being of a two-wave mixing interferometer, the wave characteristic adjusting device comprising:
    an electro-optic polarizer situated in a path of the beam of coherent electromagnetic energy;
    a polarized beam deflector situated in the path of the beam of coherent electromagnetic energy;
    a first electro-optic phase modulator;
    a second electro-optic phase modulator;
    the beam of coherent electro-magnetic energy selectively passing through the polarized beam deflector to the first electro-optic phase modulator if the electro-optic polarizer has a first specific operating characteristic;
    the electro-optic phase modulator continuously altering a wave characteristic of the beam of coherent electromagnetic energy;
    the beam of coherent electromagnetic energy selectively deflecting from the polarized beam deflector to the second electro-optic phase modulator if the electro-optic polarizer has a second specific operating characteristic;

the second electro-optic phase modulator continuously altering the wave characteristic of the beam of coherent electromagnetic energy;

the electro-optic polarizer operable to switch modes; and the wave characteristic of the beam of coherent electromagnetic energy being altered to compensate for a wave characteristic distortion caused by a scanning motion of a probe beam of the two-wave mixing interferometer.

6. The wave characteristic adjusting device of claim 5 wherein the beam of coherent electromagnetic energy is the probe beam of the two-wave mixing interferometer.

7. The wave characteristic adjusting device of claim 5 wherein the beam of coherent electromagnetic energy is a pump beam of the two-wave mixing interferometer.

8. A system for detecting a sonic energy signal associated with a manufactured object, the system comprising:

a probe beam of coherent electromagnetic energy;

a pump beam of coherent electromagnetic energy;

the probe beam being scanned across a surface of the manufactured object, wherein the probe beam is distorted by scanning;

the probe beam reflecting from the manufactured object with an altered wave characteristic indicative of a scanning motion of the probe beam;

the probe beam being directed to a two-wave mixing interferometer;

either one of the probe beam or the pump beam of coherent electromagnetic energy passing through a wave characteristic adjusting device, the wave characteristic adjusting device communicatively coupled to a wave characteristic controlling system;

the wave characteristic adjusting device operable to adjust a wave characteristic of the either one of the probe beam or pump beam, in order to compensate for distortion caused by scanning the probe beam;

a synthetic signal generator in a oath of the probe beam of coherent electromagnetic energy, so that when the probe beam passes through the synthetic signal generator, a synthetic coherent electromagnetic energy signal is added to the probe beam of coherent electromagnetic energy;

the either one of the probe beam or the pump beam being directed to the two-wave mixing interferometer; and the wave characteristic controlling system operable to direct the wave characteristic adjusting device to adjust the wave characteristic of the either one of the probe beam or the pump beam.

9. The system of claim 8, the system further comprising:

the two-wave mixing interferometer communicatively coupled to the wave characteristic controlling system, the two-wave mixing interferometer passing data to the wave characteristic controlling system; and the wave characteristic controlling system directing the wave characteristic adjusting device to adjust the wave characteristic of the either one of the probe beam or the pump beam of coherent electromagnetic energy using the data from the two-wave mixing interferometer.

10. The system of claim 8, the system further comprising:

the two-wave mixing interferometer communicatively coupled to the wave characteristic controlling system; and the wave characteristic controlling system operable to adjust a parameter of the two-wave mixing interferometer.

11. The system of claim 8 wherein the wave characteristic controlling system directs the wave characteristic adjusting device to adjust the wave characteristic of the either one of the probe beam or the pump beam of coherent electromagnetic energy using information about the synthetic signal generator.

12. The system of claim 8, the system further comprising:

a synthetic signal generator communicatively coupled to the wave characteristic controlling system; and the wave characteristic controlling system operable to direct the synthetic signal generator to add the synthetic coherent electromagnetic energy signal to the probe beam of coherent electromagnetic energy.

13. The system of claim 8, the system further comprising:

a database having information;

the database communicatively coupled to the wave characteristic controlling system; and the wave characteristic controlling system operable to direct the wave characteristic adjusting device to adjust the wave characteristic of the either one of the probe beam or the pump beam of coherent electromagnetic energy using the information from the database.

14. The system of claim 13 wherein the information in the database is information about the manufactured object.

15. The system of claim 13 wherein the information in the database is information obtained from a previous detection.

16. The system of claim 8, the system further comprising:

a representation of the manufactured object; and the wave characteristic controlling system operable to direct the wave characteristic adjusting device to adjust the wave characteristic of the either one of the probe beam or the pump beam of coherent electromagnetic energy using the representation of the manufactured object.

17. The system of claim 16 wherein the representation of the manufactured object is a computer-aided-drafting representation of the manufactured object.

18. The system of claim 8, the system further comprising:

a shape measuring device;

the shape measuring device communicatively coupled to the wave characteristic controlling system;

the shape measuring device operable to measure the shape of the manufactured object; and the wave characteristic controlling system operable to direct the wave characteristic adjusting device to adjust the wave characteristic of the either one of the probe beam or the pump beam of coherent electromagnetic energy using an information from the shape measuring device.

19. A method for testing a physical attribute of a manufactured object, the method comprising:

splitting a coherent beam of electromagnetic energy into a probe beam and a pump beam;

forming a reflected resulting beam by scanning the manufactured object with the probe beam;

determining a wave frequency adjustment required to compensate for a scanning motion of the probe beam by measuring the interaction between the pump beam and the resulting beam; and adjusting the phase of the pump beam based on determining the wave frequency adjustment by passing at least a portion of the pump beam through a continuously phase changing phase modulator to compensate for the altered wave characteristic caused by the scanning motion of the probe beam of the two wave mixing interferometer.

20. The method of claim 19 wherein the at least one wave characteristic adjusting device is situated in the optical path of the pump beam.

21. The method of claim 19 wherein the at least one wave characteristic adjusting device is situated in the optical path of the probe beam.

22. The method of claim 19, the method further comprising:
   directing the at least one wave characteristic adjusting device with a wave characteristic controlling system.

23. A method for adjusting a wave characteristic of a beam of coherent electromagnetic energy with a wave characteristic adjusting device, in order to compensate for wave distortion caused by scanning a probe beam, wherein the beam of coherent electromagnetic energy being of a two-wave mixing interferometer, the method comprising:
   selectively passing the beam of coherent electro-magnetic energy through a polarized beam deflector situated in a path of the beam of coherent electromagnetic energy to a first electro-optic phase modulator if an electro-optic polarizer situated in the path of the beam of coherent electromagnetic energy has a first specific operating characteristic;
   continuously altering a wave characteristic of the beam of coherent electromagnetic energy with the electro-optic phase modulator;
   selectively deflecting the beam of coherent electromagnetic energy from the polarized beam deflector to the second electro-optic phase modulator if the electro-optic polarizer has a second specific operating characteristic;
   continuously altering the wave characteristic of the beam of coherent electromagnetic energy with the second electro-optic phase modulator;
   the electro-optic polarizer operable to switch modes; and
   the wave characteristic of the beam of coherent electromagnetic energy being altered to compensate for a wave characteristic distortion caused by a scanning motion of a probe beam of the two-wave mixing interferometer.

24. The method of claim 23 wherein the beam of coherent electromagnetic energy is the probe beam of the two-wave mixing interferometer.

25. The method of claim 23 wherein the beam of coherent electromagnetic energy is a pump beam of the two-wave mixing interferometer.

26. A method for detecting a sonic energy signal associated with a manufactured object, the method comprising:
   scanning a probe beam of coherent electromagnetic energy across a surface of the manufactured object, wherein scanning distorts a wave characteristic of the probe beam;
   the probe beam reflecting from the manufactured object with an altered wave characteristic indicative of a scanning motion of the probe beam;
   directing the probe beam to a two-wave mixing interferometer;
   passing either one of the probe beam or the pump beam of coherent electromagnetic energy through a wave characteristic adjusting device, the wave characteristic adjusting device communicatively coupled to a wave characteristic controlling system;
   adjusting a wave characteristic of the either one of the probe beam or the pump beam with the wave characteristic adjusting device, in order to compensate for the wave distortion caused by scanning the probe beam;
   adding a synthetic coherent electromagnetic energy signal to the probe beam of coherent electromagnetic energy with a synthetic signal generator situated in a oath of the probe beam of coherent electromagnetic energy;
   directing the pump beam to the two-wave mixing interferometer; and
   directing the wave characteristic adjusting device with the wave characteristic controlling system to adjust the wave characteristic of the either one of the probe beam or the pump beam to compensate for distortion caused by scanning the probe beam.

27. The method of claim 26, the method further comprising:
   passing data to the wave characteristic controlling system from the two-wave mixing interferometer; and
   directing the wave characteristic adjusting device to adjust the wave characteristic of the either one of the probe beam or the pump beam of coherent electromagnetic energy with the wave characteristic controlling system using the data from the two-wave mixing interferometer.

28. The method of claim 26, the method further comprising:
   adjusting a parameter of the two-wave mixing interferometer with the wave characteristic controlling system.

29. The method of claim 26 wherein the wave characteristic controlling system directs the wave characteristic adjusting device to adjust the wave characteristic of the either one of the probe beam or pump beam of coherent electromagnetic energy using information about the synthetic signal generator.

30. The system of claim 26, the method further comprising:
   directing the synthetic signal generator to add the synthetic coherent electromagnetic energy signal to the probe beam of coherent electromagnetic energy, the directing being performed by the wave characteristic controlling system.

31. The method of claim 26, the method further comprising:
   directing the wave characteristic adjusting device to adjust the wave characteristic of the either one of the probe beam or pump beam of coherent electromagnetic energy with the wave characteristic controlling system, the wave characteristic controlling system using an information from a database.

32. The method of claim 31 wherein the information in the database is information about the manufactured object.

33. The method of claim 31 wherein the information in the database is information obtained from a previous detection.

34. The system of claim 26, the system further comprising:
   directing the wave characteristic adjusting device to adjust the wave characteristic of the either one of the probe beam or the pump beam of coherent electromagnetic energy with the wave characteristic controlling system, the wave characteristic controlling system using a representation of the manufactured object.

35. The method of claim 34 wherein the representation of the manufactured object is a computer-aided-drafting representation of the manufactured object.

36. The method of claim 34, the method further comprising:
   directing the wave characteristic adjusting device to adjust the wave characteristic of the either one of the probe beam or the pump beam of coherent electromagnetic energy with the wave characteristic controlling system, the wave characteristic controlling system using data from the two-wave mixing interferometer.

37. The method of claim 26, the method further comprising:
   measuring a shape of the manufactured object with a shape measuring device communicatively coupled to the wave characteristic controlling system; and
   directing the wave characteristic adjusting device to adjust the wave characteristic of the either one of the probe beam or the pump beam of coherent electromagnetic energy with the wave characteristic controlling system, the wave characteristic controlling system using an information from the shape measuring device.

38. The method of claim 37, the method further comprising:

directing the wave characteristic adjusting device to adjust the wave characteristic of the either one of the probe beam or pump beam of coherent electromagnetic energy with the wave characteristic controlling system, the wave characteristic controlling system using the data from the two-wave mixing interferometer.

\* \* \* \* \*